United States Patent
Peters

(10) Patent No.: US 11,707,598 B2
(45) Date of Patent: Jul. 25, 2023

(54) URINARY CATHETER CADDY AND DISPENSER

(71) Applicant: Monali M. Peters, Rock Springs, WY (US)

(72) Inventor: Monali M. Peters, Rock Springs, WY (US)

(*) Notice: Subject to any disclaimer, the term of this patent is extended or adjusted under 35 U.S.C. 154(b) by 172 days.

(21) Appl. No.: 16/818,735

(22) Filed: Mar. 13, 2020

(65) Prior Publication Data
US 2021/0283367 A1 Sep. 16, 2021

(51) Int. Cl.
*A61M 25/00* (2006.01)
*B65D 83/02* (2006.01)

(52) U.S. Cl.
CPC ......... *A61M 25/002* (2013.01); *B65D 83/02* (2013.01); *A61M 2209/082* (2013.01); *A61M 2209/10* (2013.01)

(58) Field of Classification Search
CPC .............. B65D 83/02; A61M 2209/10; A61M 2209/082; A61M 25/002
USPC ................................. 206/364, 443; 220/253
See application file for complete search history.

(56) References Cited

U.S. PATENT DOCUMENTS

| | | | | |
|---|---|---|---|---|
| 6,036,067 A | * | 3/2000 | Alcorn | A01K 77/00 206/315.11 |
| 6,062,382 A | * | 5/2000 | Czerkie | A01K 97/08 206/443 |
| 2007/0051650 A1 | * | 3/2007 | Carlozzi | B65D 77/02 206/443 |
| 2011/0114520 A1 | * | 5/2011 | Matthison-Hansen | A61M 25/0111 206/364 |

* cited by examiner

*Primary Examiner* — Steven A. Reynolds
(74) *Attorney, Agent, or Firm* — Robert R. Mallinckrodt

(57) ABSTRACT

A urinary catheter caddy for storing a plurality of packages of urinary catheters and for holding a selected one of the plurality of packages for dispensing of the urinary catheter therefrom includes a caddy body forming a storage space sized to receive and hold a plurality of packages of urinary catheters. An access opening extends from outside the caddy body into the storage space so a user can select one of the urinary catheter packages and pull an openable end of the selected package through the access opening with the opposite end of the package remaining in the storage space. The package is opened to expose a portion of the urinary catheter and an opened portion of the package is held by a package material holder so the catheter can be pulled by the exposed portion from the opened package without contaminating the catheter.

20 Claims, 11 Drawing Sheets

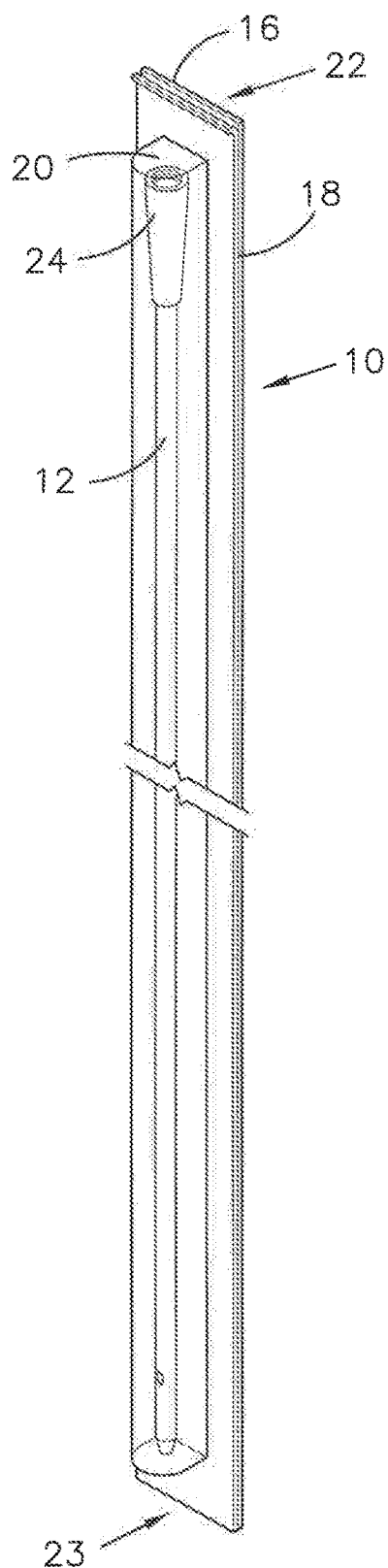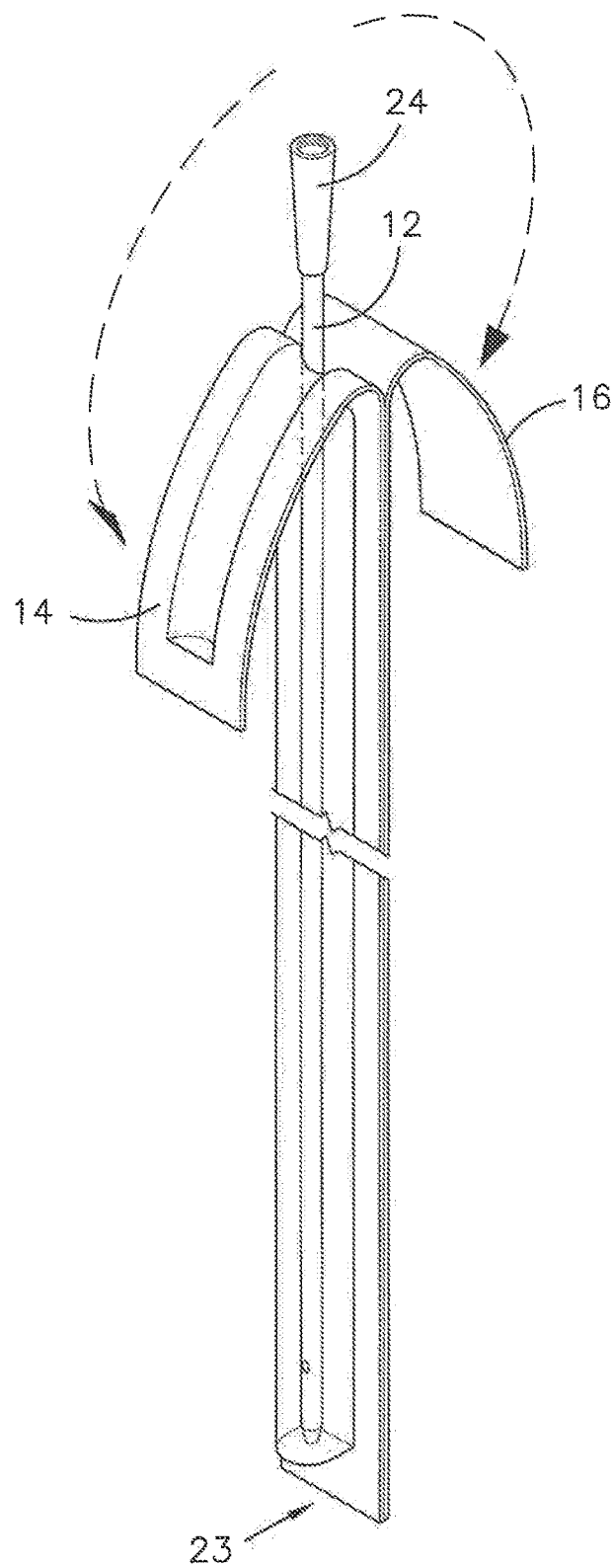
FIG. 1
(Prior Art)
FIG. 2
(Prior Art)

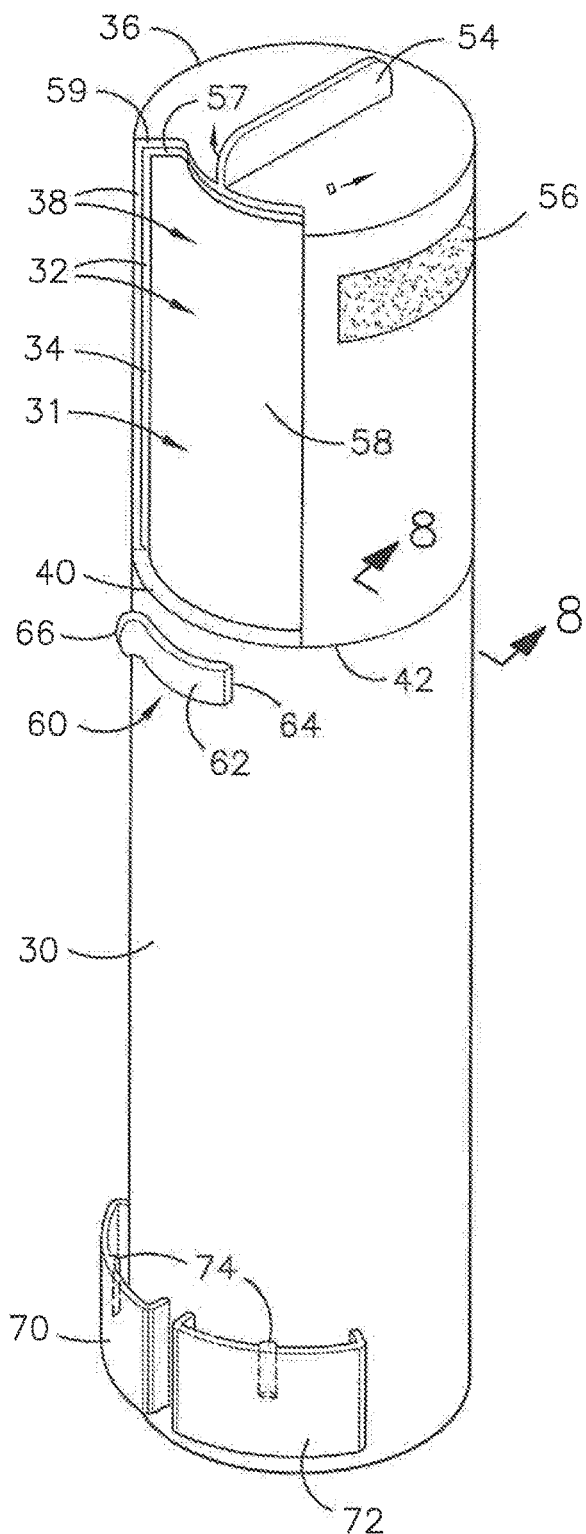
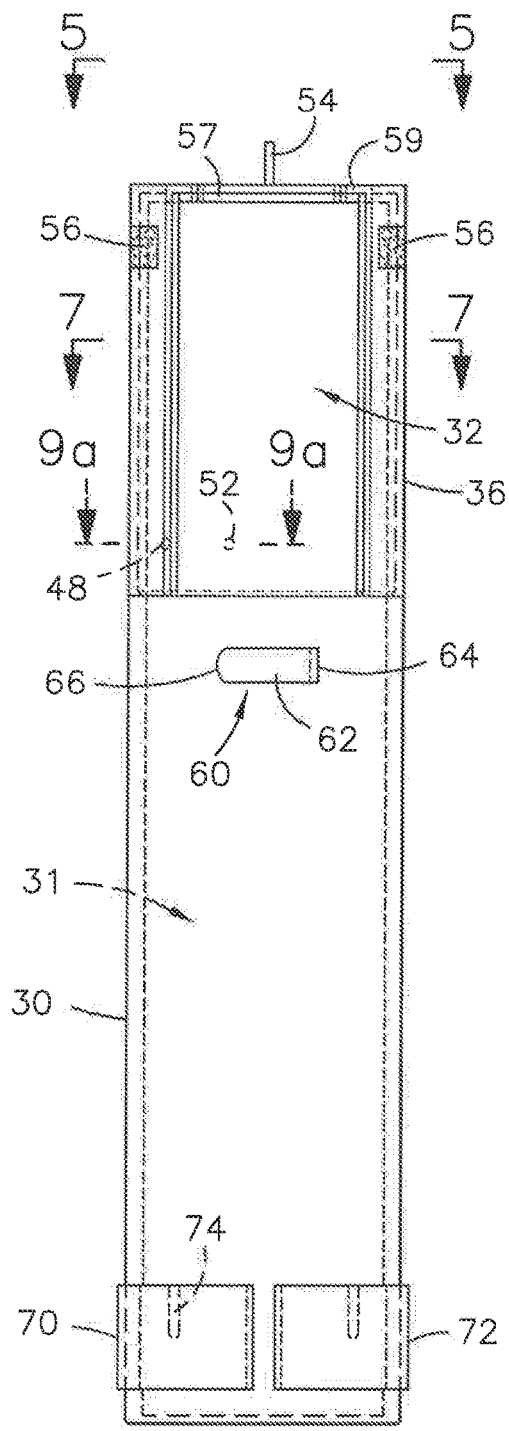
FIG. 3
FIG. 4

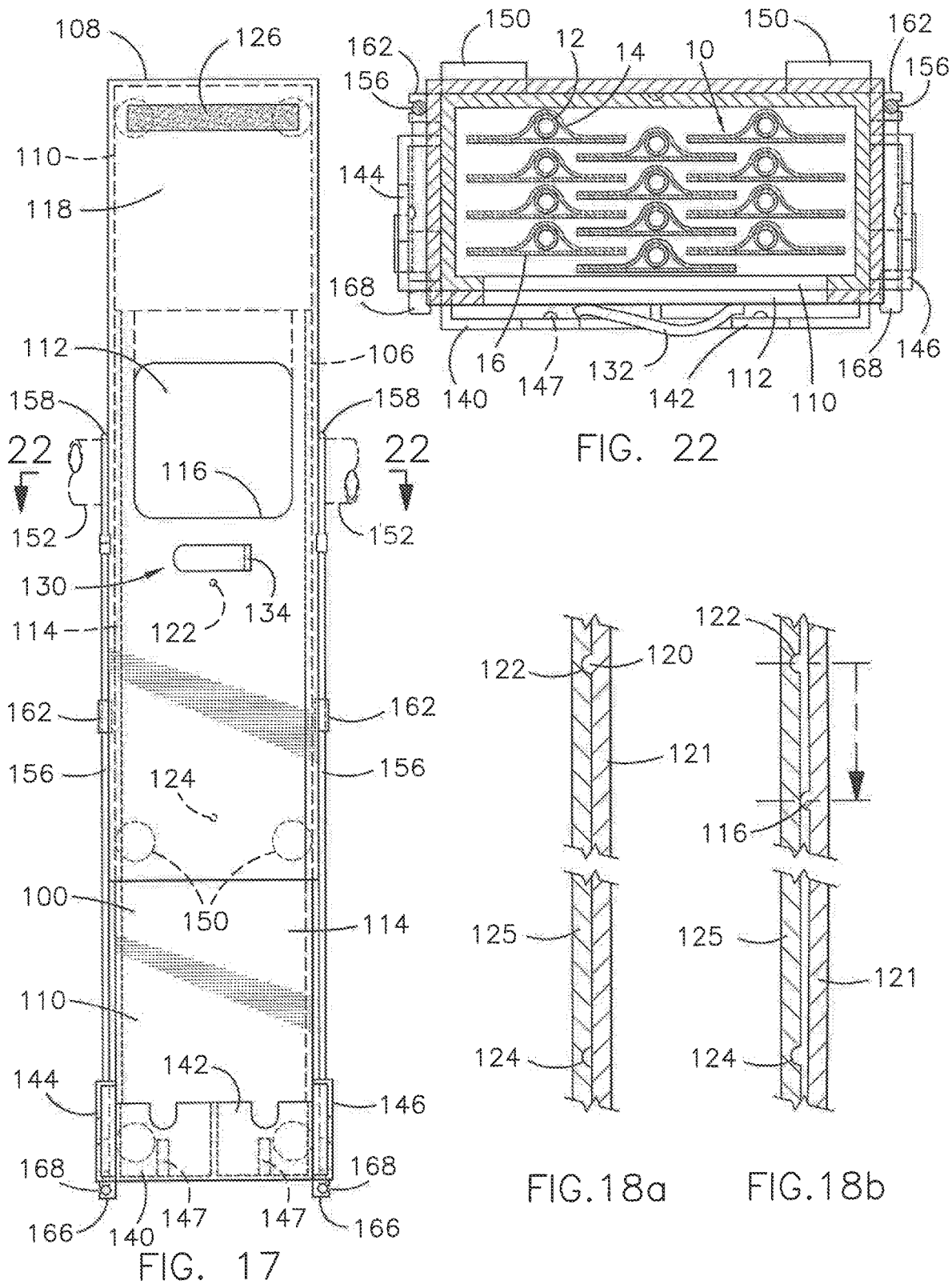

URINARY CATHETER CADDY AND DISPENSER

BACKGROUND

Field of the Invention

The present invention relates to the storage, carrying, and dispensing of urinary catheters so that such catheters are available for use by a user when needed.

Background of the Invention

Various medical conditions, such as multiple sclerosis, paralyzed bladder, spinal cord injuries, paraplegia, and quadriplegia, require catheterization of the bladder either permanently, on an occasional basis, or each time the person needs to urinate. In the latter case, the person needs to self-catheterize or be catheterized each time the person has to urinate, which means that the person or care giver inserts the catheter through the urethra and into the bladder to allow the bladder to drain, and then removes the catheter. This requires that the person have a catheter available each time catheterization is needed. Often this requires the person to carry one or more urinary catheters with him or her, particularly when the person leaves home or other locations where such catheters may be easily stored in an accessible location. Further, even when home or at a location where the person spends time, it is important to have a convenient storage space for such catheters.

Urinary catheters, also referred to as straight catheters, are elongate, and while resilient, usually maintain a substantially straight shape when unrestrained and when packaged. Urinary catheters for use in males are generally about sixteen to eighteen inches in length and for use in females are general about nine to twelve inches in length. Urinary catheters are usually packaged individually in sterile condition in a sealed sterile package which is opened when the catheter is needed and the catheter is carefully removed from the package and used. FIGS. 1 and 2 are pictorial views of a package 10 containing a urinary catheter 12. FIG. 1 shows the package closed as sold containing a sterile urinary catheter 12 therein and FIG. 2 shows the package partially opened. Such packages generally allow the catheters to maintain their elongate condition and comprise a transparent plastic side 14 and an opaque paper like side 16. The opaque paper like side of the package, while bendable, is generally flat and shape retaining. The plastic side 14 and the paper like side 16 are sealed together along their edge portions 18 with the catheter 12 sealed inside. The plastic side is sealed along the flat edge portions of the paper like side and generally forms a channel 20 therein around the catheter 12. The package is generally openable at an openable end 22 where the plastic side 14 and paper like side 16 are not sealed together right along the end edge so the end edges can be easily separated and the two sides can then be pulled apart to separate and peel the sides away from one another to open the package progressively from the openable end 22 toward the opposite end 23 to expose the catheter as shown in FIG. 2. Most urinary catheters include a fitting or bell 24 on one end, which is the end of the catheter that extends from the urethra when the catheter is inserted into the urethra. This fitting and end of the catheter adjacent the fitting is not inserted into the urethra so can be held by a user to manipulate the catheter when removing the catheter from the package and when inserting the catheter into the urethra without worrying about keeping that end portion sterile. The fitting 24 is usually provided to be used as a connection for a syringe when needed to flush the bladder by inserting fluid from the syringe through the fitting and the catheter into the bladder. With the catheter in the package, this fitting 24 will be located in channel 20 adjacent the openable end 22 of the package. When the plastic and paper like sides are fully separated to the opposite end of the package, not shown, the package is fully opened and the plastic or paper like side, usually the plastic channeled side which cradles the catheter, can be carefully positioned on a horizontal surface with the catheter resting in the plastic package side with the plastic package side between the catheter and the surface to keep it sterile. Care needs to be taken to keep the catheter resting in the sterile package side. The catheter can then be picked up for use by the user, such as the person performing self-catheterization or a care giver performing the catheterization, with the user being careful not to let the catheter touch any nonsterile surface. Usually the user will have carefully washed their hands and/or gloved with sterile gloves prior to picking up the catheter from the opened package.

Alternately, rather than completely opening the catheter package, the package can be opened only part way from the openable end toward the opposite end as shown in FIG. 2 and the catheter can then be pulled from the package with the user holding such opposite end of the package. However, the user has to hold the opposite end of the package while removing the catheter and then has the empty package in the user's hand to dispose of before that hand is available to help with the catheter insertion. Further, the hand holding the catheter package will not be sterile after holding the package for removal of the catheter and it is difficult to wash or glove that hand while the other hand is holding the removed sterile catheter. In any situation it is generally important to keep the parts of the catheter to be inserted into the body sterile, but this can be difficult in many situations. Sterile gloves are very often used when holding and manipulating the catheter, with care being taken not to touch nonsterile surfaces with the gloves until after catheterization is completed.

In addition, a person needing catheterization usually does not want to make that need public. However, it can be difficult for a person to carry a supply of even a few separate packages of urinary catheters with them so that they are available when needed but not obvious. Further, even at home, it can be difficult to organize a supply of urinary catheter packages and have such packages available for easy access and easy dispensing of the catheter from the package. This is true also for medical facilities such as clinics and hospitals where urinary catheters may be needed so a supply of such catheters should be available for easy dispensing.

SUMMARY OF THE INVENTION

According to the invention, a caddy is provided for holding a plurality of unopened packages of urinary catheters within the caddy out of public sight. The caddy provides a storage space for holding a plurality of urinary catheter packages and has an access opening through which a urinary catheter package in the storage space can be accessed by a user when a urinary catheter is needed. A urinary catheter package is selected from the plurality of urinary catheter packages in the storage space and is partially removed from the storage space through the access opening so as to expose the openable end and an intermediate portion of the urinary catheter package adjacent the openable end of the package in a position outside the caddy where the openable end of the package can be opened by the user. The end of the package opposite the openable end and the intermediate portion of the package adjacent that opposite end will remain in the storage space so as to be held by the caddy with the openable end of the package extending from the access opening in the caddy. In such position, the urinary catheter package can be partially opened by a user. The user can grasp the edges of the package sides at the openable end of the package, pull the sides at the openable end apart and continue to pull apart and separate the sides of the urinary catheter package from the openable end toward the opposite end to expose a portion of the urinary catheter in the opened portion of the urinary catheter package. When the urinary catheter package is partially opened by a user, the side of the package on the side of the exposed portion of the urinary catheter away from the container, usually the paper like side of the package, is pulled toward the end of the container away from the openable end of the package and is secured in a package material holder positioned between the access opening and the end of the caddy away from the openable end of the package so as to hold such side of the opened package in a manner to ensure that the portion of the urinary catheter package remaining in the storage space remains in place in the storage space. The opened side of the urinary catheter package on the side of the exposed catheter toward the container, usually the plastic side of the package, will usually remain between the exposed catheter and the caddy to protect the exposed end and adjacent portion of the catheter from contact with the caddy. In this way, the exposed portion of the catheter is maintained in sterile condition as it remains extended from the caddy and is in a position where it can be easily grasped by the user. With the opposite end portion of the package held in the caddy, the user can grasp the exposed end of the catheter and pull the catheter from the opposite end portion of the package held in the storage space to completely remove the catheter from the package without contaminating the catheter while removing the catheter. The user does not have to manually hold the opposite end portion of the package when removing the catheter and is not left with an empty package in the user's hand after the catheter has been removed. The empty package remains in the caddy for later removal. The user can thus fully wash and/or glove both hands before removing the catheter from the opened package held in the caddy without touching a non-sterile surface. The user thus has both hands immediately available for use in manipulating and inserting the catheter.

In inserting a urinary catheter into the body it is generally desirable to lubricate the end of the catheter inserted. This can be done by applying a lubricating gel to the insertion end of the catheter. Such gel is available in sterile packets and, as presently used, the packet is opened and sterile gel is squeezed from the packet onto the end of the catheter. With the present invention, however, the caddy can be provided with a compartment or pocket for holding a sterile gel packet in open condition so the insertion end of the catheter can be inserted through the open end of the gel packet into the gel without touching the package, and can be removed from the gel packet, again, without touching the package or otherwise contaminating the catheter.

In addition, in some situations, it is desirable to use a disinfecting wipe to wipe and disinfect the area around the urethra prior to insertion of the catheter. With the present invention, the caddy can be provided with a compartment or pocket for holding in an open condition a packet containing a disinfecting wipe so that the disinfecting wipe can be easily removed from the packet for use.

With the urinary catheter package held in and the openable end of the catheter package extending through the access opening in the storage space, an open gel packet held in the gel packet pocket, and an open disinfecting wipe packet held in the disinfecting wipe packet pocket, the openable end of the catheter package can be partially opened by the user without touching the catheter, and the material of the opened end of the package on the side of the exposed catheter away from the caddy placed in the package material holder. The user can then glove so that when using sterile gloves, only the catheter itself needs to be held by the gloved user and removed from the package, dipped into the open gel pack, and placed into the urethra without the catheter or the gloved user's hand having to touch non-sterile surfaces during such procedure. The sterile wipe, if used, can be taken from the open sterile wipe packet and used to wipe the area around the urethra either before or after gloving. For a completely sterile procedure, the user can first glove with sterile gloves and remove the sterile wipe from the open sterile wipe packet and use the wipe to clean the area around the urethra. The user would then remove those gloves and re-glove with new sterile gloves to then grasp the exposed end of the catheter and carefully remove the catheter from the catheter package, carefully insert the end of the catheter into the open gel packet, carefully remove the end of the catheter from the gel packet, and move to inserting the catheter into the urethra. The caddy of the invention provides an easy way for a user to store and/or carry packages of urinary catheters and to easily remove a urinary catheter from its package when the catheter is needed.

The caddy can be provided in various shapes and sizes, such as in a cylindrical shape or in a rectangular shape, and can be configured to rest on a substantially flat horizontal surface, hung on a handrail or drawer or door edge, or be hung on a wall or other surface bracket. Further, the access opening of the caddy can be closed for enclosed storage and carrying of the catheter packages and opened for easy access to the catheter packages and catheters when needed.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 1 is a pictorial view of a closed package containing a urinary catheter as it is usually supplied to a user;

FIG. 2 is a pictorial view of the package of FIG. 1 containing the urinary catheter but showing the package partially opened;

FIG. 3 is a pictorial view of a cylindrically shaped catheter caddy of the invention in open condition showing the opening into the inside of the caddy;

FIG. 4 is a front elevation of the catheter caddy of FIG. 3;

FIG. 17 is a front elevation of the catheter caddy of FIG. 14 in open condition;

FIG. 18a is a fragmentary vertical section taken on the line 18a-18a of FIG. 15 and drawn to a larger scale showing the caddy in closed condition and showing the back walls of the main caddy body and the outer caddy body with a holding projection received in a holding recess to hold the catheter caddy in closed condition;

FIG. 18b is a fragmentary vertical section similar to that of FIG. 18a but showing the caddy in an intermediate condition between the closed condition of FIG. 18a to an intermediate condition between closed and open conditions with the holding projection not received in a holding recess;

FIG. 22 is a horizontal section of the rectangular caddy taken on the line 22-22 of FIG. 17, but not showing the bar from which the caddy can be hung.

Reference will now be made to the exemplary embodiments illustrated, and specific language will be used herein to describe the same. It will nevertheless be understood that no limitation of the scope of the invention is thereby intended.

DETAILED DESCRIPTION OF ILLUSTRATED EMBODIMENTS

Figure 5:
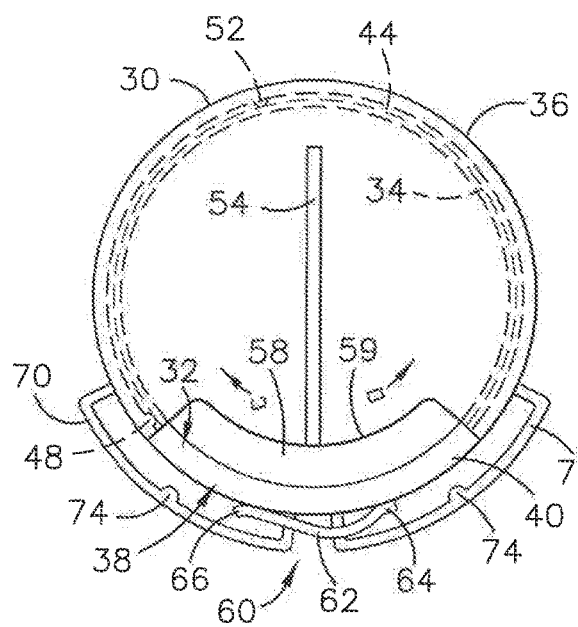
FIG. 5 is a top view of the catheter caddy of FIG. 4 in open condition.
Figure 6:
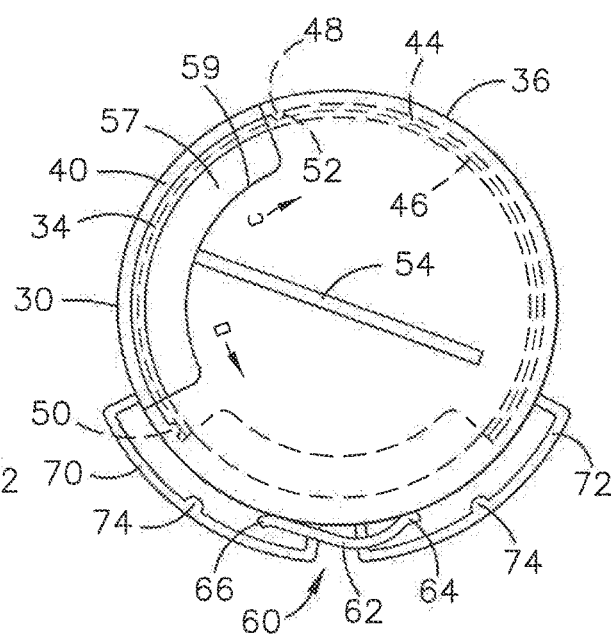
FIG. 6 is a top view similar to FIG. 5, but showing the caddy in closed condition.

The invention provides a caddy for storing and carrying a plurality of packages of urinary catheters, and for dispensing a urinary catheter from its package. In one embodiment of the invention, the caddy may be of cylindrical shape as shown in FIGS. 3-13, having a cylindrical caddy body 30 forming a catheter package storage space 31 within the caddy body and with a caddy body access opening 32 in a reduced outside diameter portion 34 of the caddy body 30, which, with the vertical orientation of the caddy shown in the drawings, will be referred to as the upper portion 34 of the cylindrical caddy body 30. The caddy body access opening 32 provides access from outside the caddy body 30 to the catheter package storage space 31 within the caddy body. A rotatable cap 36 is provided over the upper portion 34 of the cylindrical caddy body 30. Cap 36 is rotatable with respect to cylindrical caddy body 30 and has a cap opening 38 corresponding in size substantially to caddy body opening 32 in the upper caddy body portion 34 so that cap 36 can be rotated between a closed position wherein cap 36 extends over caddy body opening 32 to close caddy body opening 32 as shown in FIG. 6, and an open position wherein cap opening 38 is substantially aligned with caddy body opening 32 as shown in FIGS. 3, 4, 5, and 7. With the reduced outside diameter upper portion 34 of the illustrated embodiment of cylindrical caddy body 30, a step 40 is formed in cylindrical caddy body 30 at the lower edge 42 of cap 36 to accept the wall thickness of the cap 36. The outside diameter of cap 36 in this illustrated embodiment will be the same as the outer diameter of the lower portion of cylindrical caddy body 30. In this way, for esthetic purposes, the entire length of the caddy will have the same outside diameter.

Figure 7:
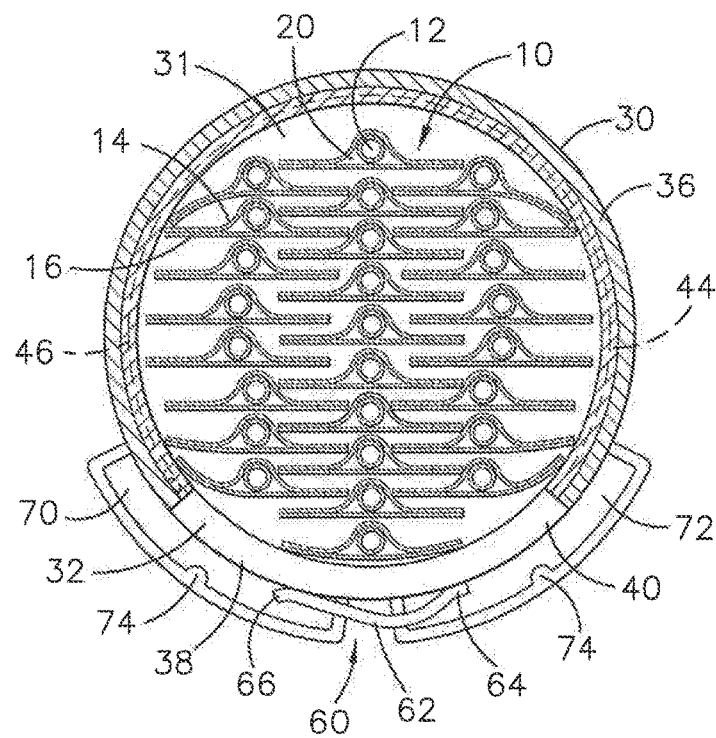
FIG. 7 is a horizontal section taken on the line 7-7 of FIG. 4 and drawn to a slightly larger scale showing a plurality of catheter packages, in section, within the cylindrically shaped caddy.
Figure 8:
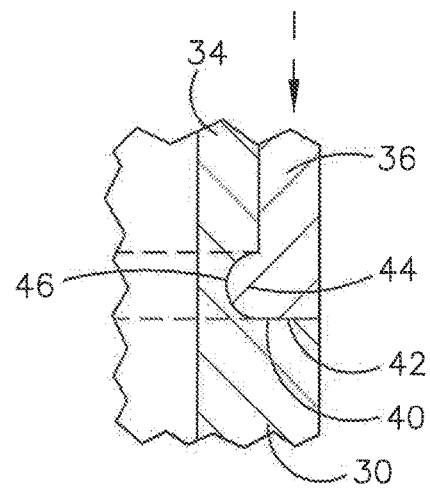
FIG. 8 is a fragmentary vertical section taken on the line 8-8 of FIG. 3 and drawn to a larger scale showing the connection of the caddy body cap to the cylindrical caddy body.

In order to attach cap 36 to cylindrical caddy body 30, the lower portion of cap 36 can be provided with an internal ridge 44, FIG. 8, around its lower portion, shown as adjacent to lower edge 42, which extends between the sides of cap opening 38 and which mates with body groove 46 in the upper portion 34 of cylindrical caddy body 30, shown as just above step 40, extending around the upper portion 34 between the sides of caddy body opening 32. During assembly of the caddy, cap 36 is pushed over upper portion 34 of cylindrical caddy body 30 with the lower portion of cap 36 flexing slightly so that internal ridge 44 slides over upper portion 34 of cylindrical caddy body 30 into body groove 46 to hold cap 36 on the upper portion 34 of cylindrical caddy body 30. Ridge 44 can slide in groove 46 to allow cap 36 to rotate with respect to cylindrical caddy body 30. When cap 36 is rotated so that cap opening 38 is substantially aligned with caddy body opening 32 as shown in FIGS. 3, 4, 5, and 7, the caddy is in open position so a user can reach through openings 38 and 32 into caddy body 30 and catheter package storage space 31 so can insert catheter packages 10 into caddy body 30 or remove catheter packages 10 from inside caddy body 30.

Figure 9A:
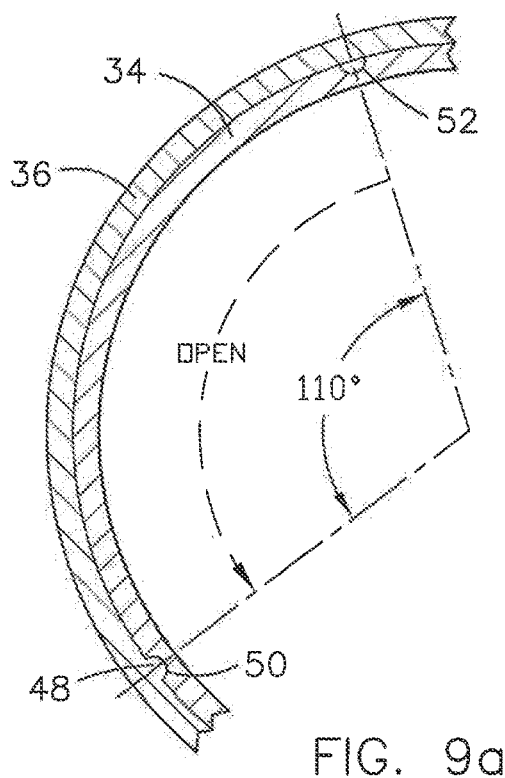
FIG. 9a is a fragmentary horizontal section taken on the line 9a-9a of FIG. 4 and drawn to a larger scale with the caddy in open condition showing a holding projection received in a holding recess to hold the catheter caddy in open condition.
Figure 9B:
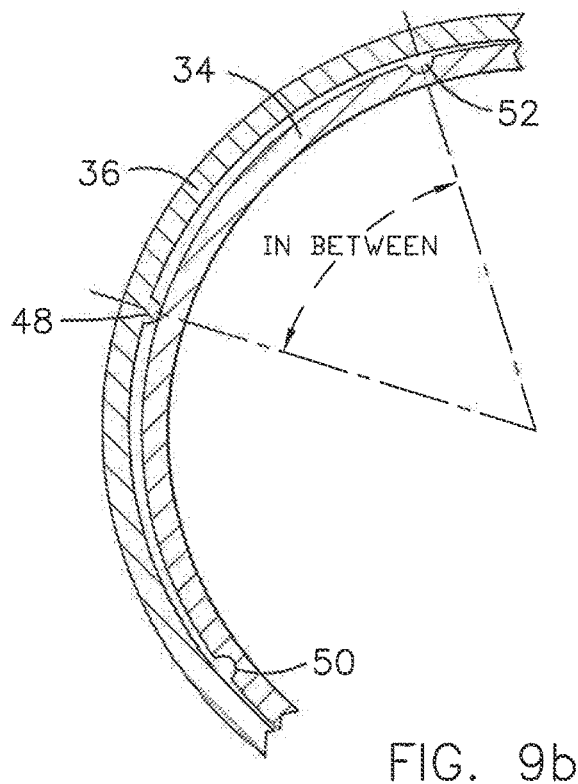
FIG. 9b is a fragmentary horizontal section similar to that of FIG. 9a but showing the caddy cap rotated 45 degrees from the open position in FIG. 9a to a half open condition with the holding projection not received in a holding recess.
Figure 9C:
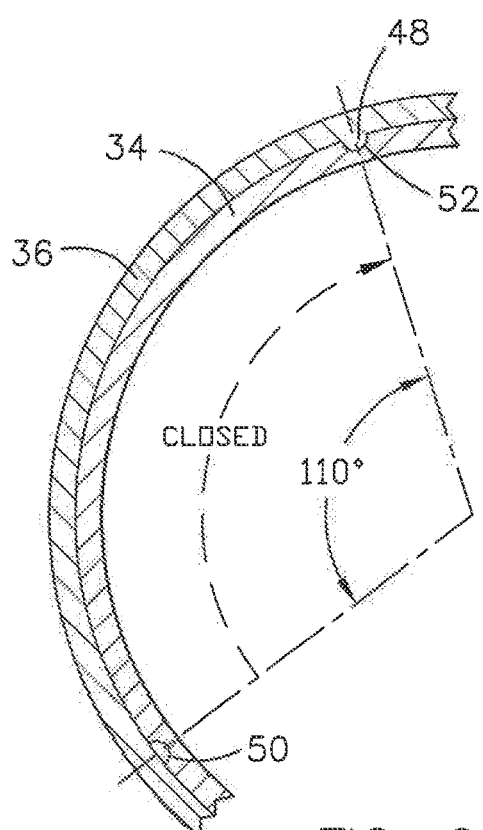
FIG. 9c is a fragmentary horizontal section similar to that of FIG. 9a but showing the caddy cap rotated 90 degrees from the open position in FIG. 9a to a closed condition showing the holding projection received in a holding recess to hold the catheter caddy in closed condition.

It will generally be desirable to be able to hold cap 36 in the rotated open or rotated closed position. For this purpose, cap 36 can be provided with an internal projection 48, FIGS. 9a, 9b, and 9c, above internal ridge 44, and the upper portion 34 of cylindrical caddy body 30 can be provided with a pair of associated indentations 50 and 52, see also FIG. 4, so that when cap 36 is rotated to open position as shown in FIG. 9a, projection 48 fits into indentation 50 to hold cap 36 in open position. When cap 36 is rotated to closed position as shown in FIG. 9c, projection 48 fits into indentation 52 to hold cap 36 in closed position. Again, with cap 36 having cap opening 38, cap 36 can flex and expand slightly at the location of projection 48 when cap 36 is rotated. FIG. 9b shows cap 36 during rotation intermediate between open and closed positions with projection 48 between indentations 50 and 52. Cap 36 can be provided with a top tab 54, FIGS. 3-6, as a handle to rotate cap 36 and/or with nonslip material 56 to form finger grips on opposite sides of cap 36 which can be grasped by a user to rotate cap 36.

With the cylindrical caddy embodiment illustrated, the top of caddy body opening 32 can extend partially into the top 57 of caddy body 30 as shown at 58, FIGS. 3, 5, 10-12, and cap opening 38 can similarly extend into the top of cap 36 as shown at 59, FIGS. 3, 5, 6, and 10-13 to enlarge the opening into the storage space 31 in caddy body 30 when the caddy is in open condition as shown in FIGS. 3, 5, and 10-12. This can ease insertion and withdrawal of catheter packages into and out of the caddy storage space 31.

A package material holder 60 is attached to cylindrical caddy body 30 centered below caddy body opening 32. As illustrated, the package material holder 60 may take the form of a spring tab 62 attached at one end 64 to cylindrical caddy body 30 centered below caddy body opening 32. Spring tab 62 is biased against cylindrical caddy body 30 with end 66 tapered away from against cylindrical caddy body 30 to form an entrance for sheet material such as paper or plastic to be inserted and held between spring tab 62 and cylindrical caddy body 30. If needed, the surface of spring tab 62 and/or cylindrical caddy body 30 against which spring tab 62 abuts can be roughened or otherwise shaped, such as with intervening ridges or tabs, to reduce sliding of the sheet material between the two, except when forced.

In addition, cylindrical caddy body 30 may be provided with one or more, and preferably two, pockets 70 and 72 in a convenient location such as at the bottom portion of cylindrical caddy body 30 as shown in FIGS. 1-4 and 10-12, below caddy body opening 32. These pockets will be sized to receive and hold an open packet of sterile catheter lubrication gel and an open sterile packet of a cleaning wipe. Pocket 70 may be about an inch and one half wide with about one quarter inch between cylindrical caddy body 30 and the outside wall of the pocket to hold a standard sterile gel packet in a slightly squeezed open condition and pocket 72 may be about two inches wide with about one quarter inch between cylindrical caddy body 30 and the outside wall of the pocket to hold a standard cleaning wipe packet in a slightly squeezed open condition. While if the width of the respective pockets is slightly narrower than the width of the packet to be held therein so that the packet needs to be squeezed to be inserted and be held in an open condition, the lubricating gel packet will generally remain in the pocket when the catheter end with lubricating gel is withdrawn from the packet or the sterile wipe packet will generally remain in the pocket when the sterile wipe is pulled from the packet, the inside of the pocket can be roughened or otherwise shaped, such as with a ridge or bar 74, to more securely hold the packet within the pocket when the catheter or wipe is withdrawn from the packet. With such rib or bar holding the packet, the pockets can be made the same size and either type of packet can be opened and placed in either pocket.

Figure 11:
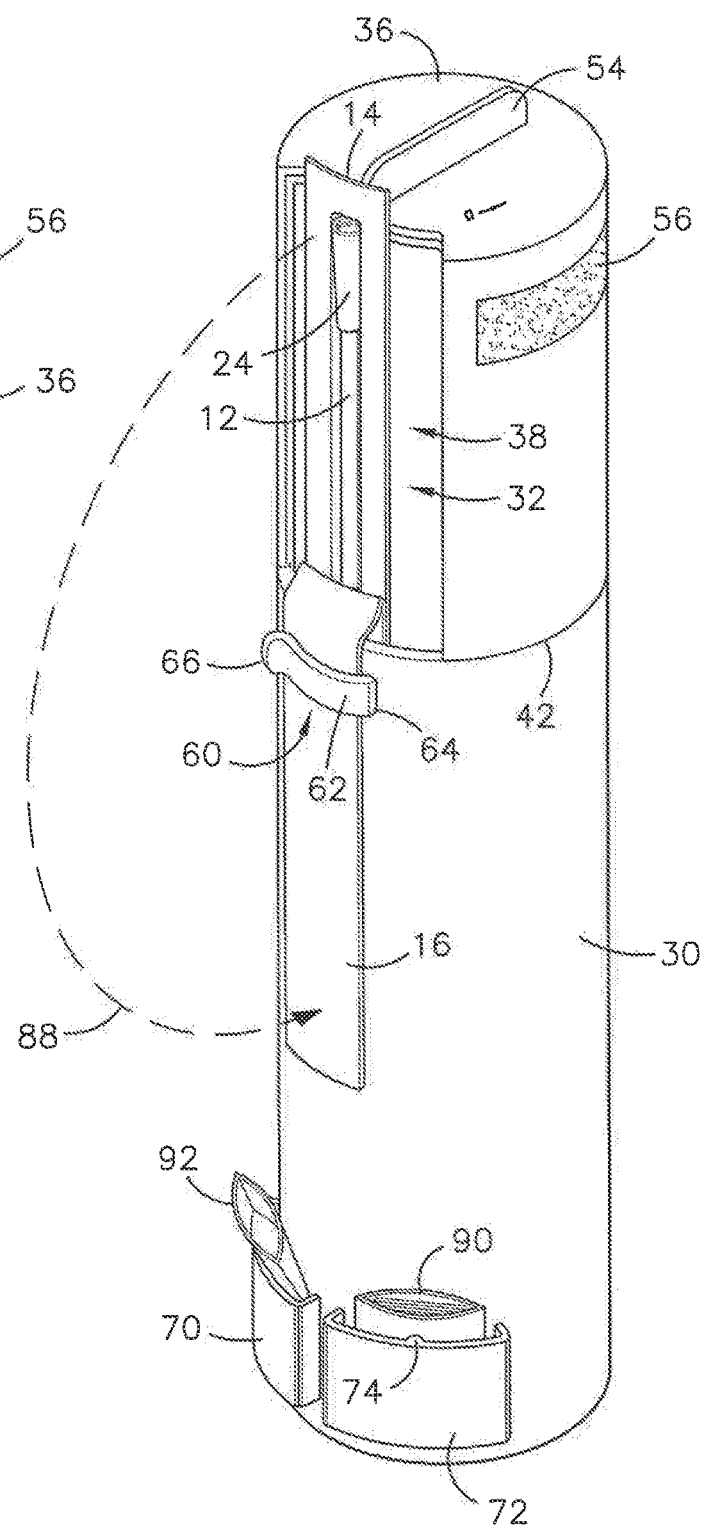
FIG. 11 is a pictorial view of the cylindrically shaped caddy of FIG. 10 with the catheter package shown partially open and the side of the catheter package away from the caddy body inserted into and held by a package material holder.
Figure 12:
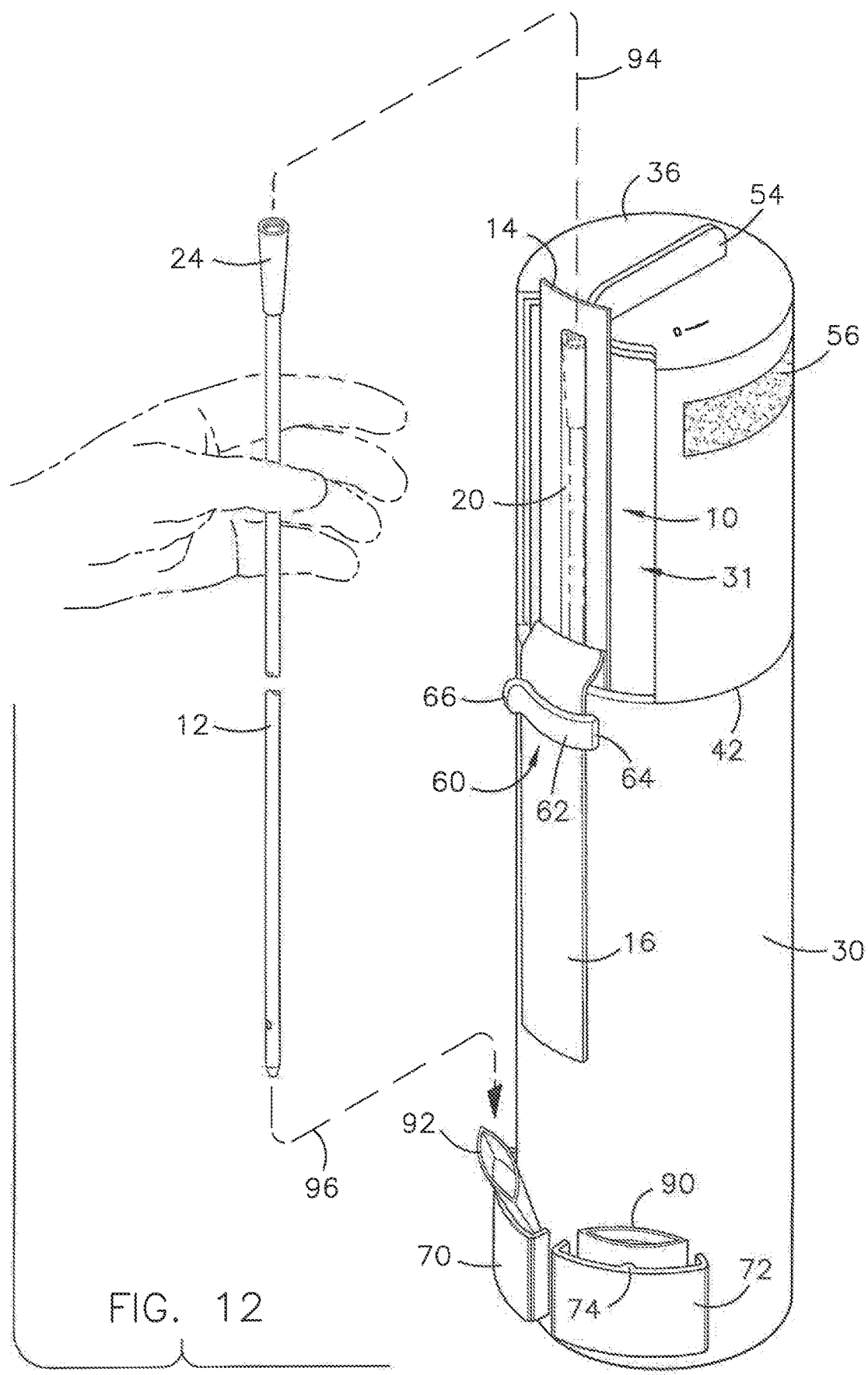
FIG. 12 is a pictorial view of the cylindrically shaped caddy as shown in FIG. 11 with the catheter package shown partially open and the side of the catheter package away from the caddy body inserted into and held by the package material holder as shown in FIG. 11, and showing the catheter in an alternate position removed from the catheter package and the caddy and indicating by the broken line arrow how the catheter is removed from its package and how the insertion end of the catheter can be inserted into an open lubricating gel package in a lubricating gel package holding pocket.
Figure 13:
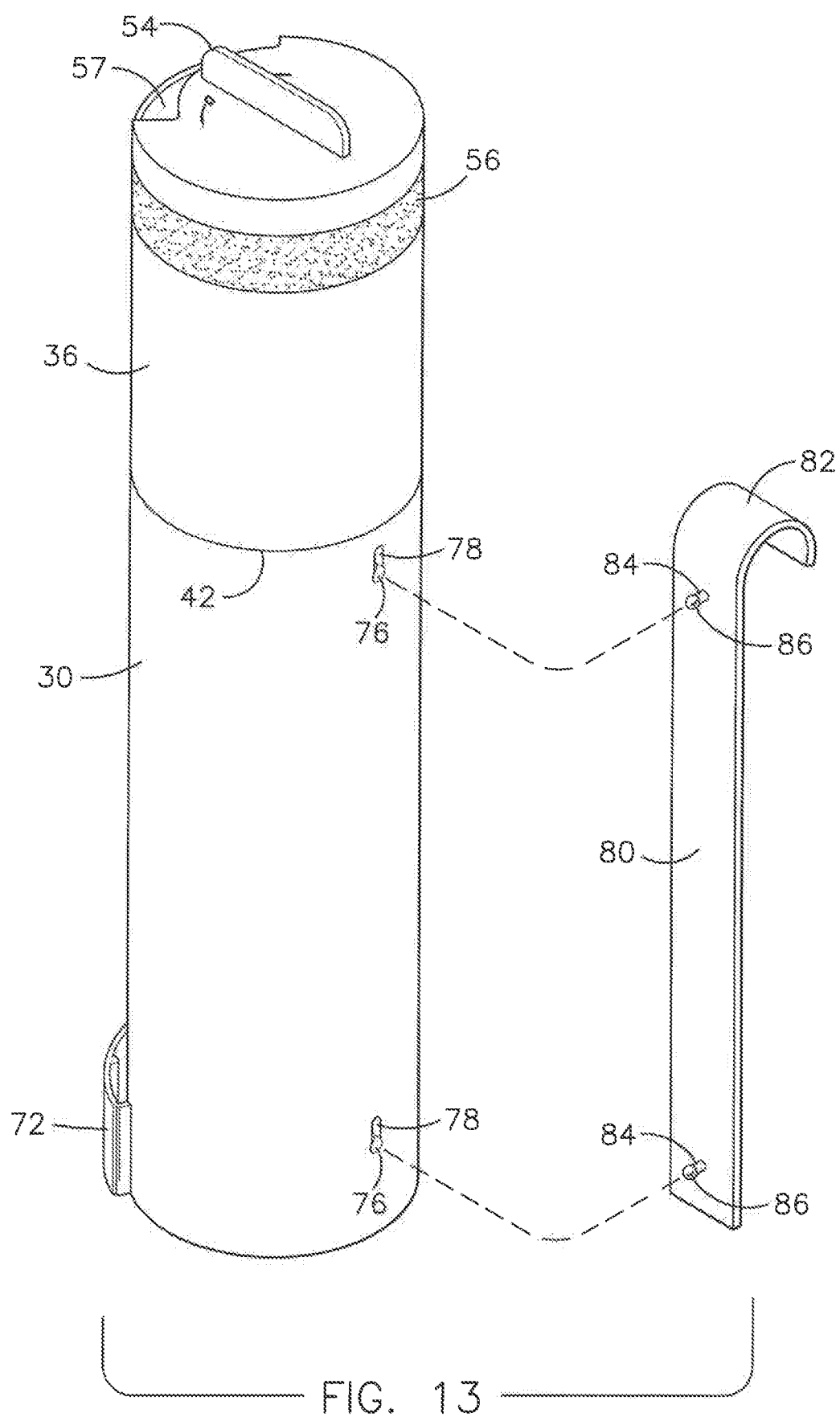
FIG. 13 is a pictorial view of the cylindrically shaped caddy of FIG. 10 rotated to show the back of the caddy and an example of a hanger that can be attached to the caddy body for hanging the caddy body when and if desired.

The cylindrical caddy can be stored and carried in any orientation, but will generally be held and used in vertical orientation as shown in FIGS. 3-13, but can be kept, held, and used in various other orientations. In addition, the cylindrical caddy can be provided with attachments for mounting to a surface or to a holder. For example, FIG. 13 shows a pair of mounting holes 76 through the back of cylindrical caddy body 30 which include slot extensions 78 extending upwardly therefrom. A bracket 80 having a hook formation 82 at the top thereof includes posts 84 with heads 86 extending therefrom and spaced the same distance apart as holes 76. Holes 76 are sized to accept heads 86 and posts 84 therethrough and slot extensions 78 are sized to accept posts 84 but not heads 86. Therefore, bracket 80 can be held to align posts 84 with holes 76 and posts 84 with heads 86 can be inserted into holes 76. Bracket 80 can then be moved toward the top of cylindrical caddy body 30 so that posts 84 slide into slit extensions 78 with post heads 86 inside cylindrical caddy body 30. The caddy can then be held securely by bracket 80, which can be hung by hook formation 82 over a bar, such as a horizontal bar in a bathroom or top of a door or drawer or other horizontal support. Additionally, posts 84 with heads 86 can be installed in a wall or other support and cylindrical caddy body 30 can be hung on such posts when desired. For example, such posts can be installed in a bathroom or doctor's office or other location, such as a medical supply cart when urinary catheters need to be readily available for use.

To prepare the caddy for use, cap 36 is rotated to open position where cap opening 38 is aligned with caddy body opening 32 so access to the inside of cylindrical caddy body 30 is provided. Packages 10 of catheters can then be inserted through aligned openings 38 and 32 and arranged in cylindrical caddy body 30. The catheter packages 10 will be oriented with the openable end 22 of the package 10 toward the top of the cylindrical caddy body 30 which has the opening therethrough. FIG. 7 is a section through the top portion of the caddy showing a plurality, here twenty six, of packages 10 of urinary catheters 12 positioned in caddy body 30 for storage and carrying of such packages. The catheter packages 10 will preferably be arranged with the opaque paper like side 16 facing the aligned openings 32 and 38, although they could be arranged oppositely. Once catheter packages 10 are inserted into catheter body 30 through aligned cap opening 38 and caddy opening 32, the user will generally rotate cap 36 to closed position to close caddy opening 32 for storage and carrying of the catheter packages 10 in a closed caddy.

Figure 10:
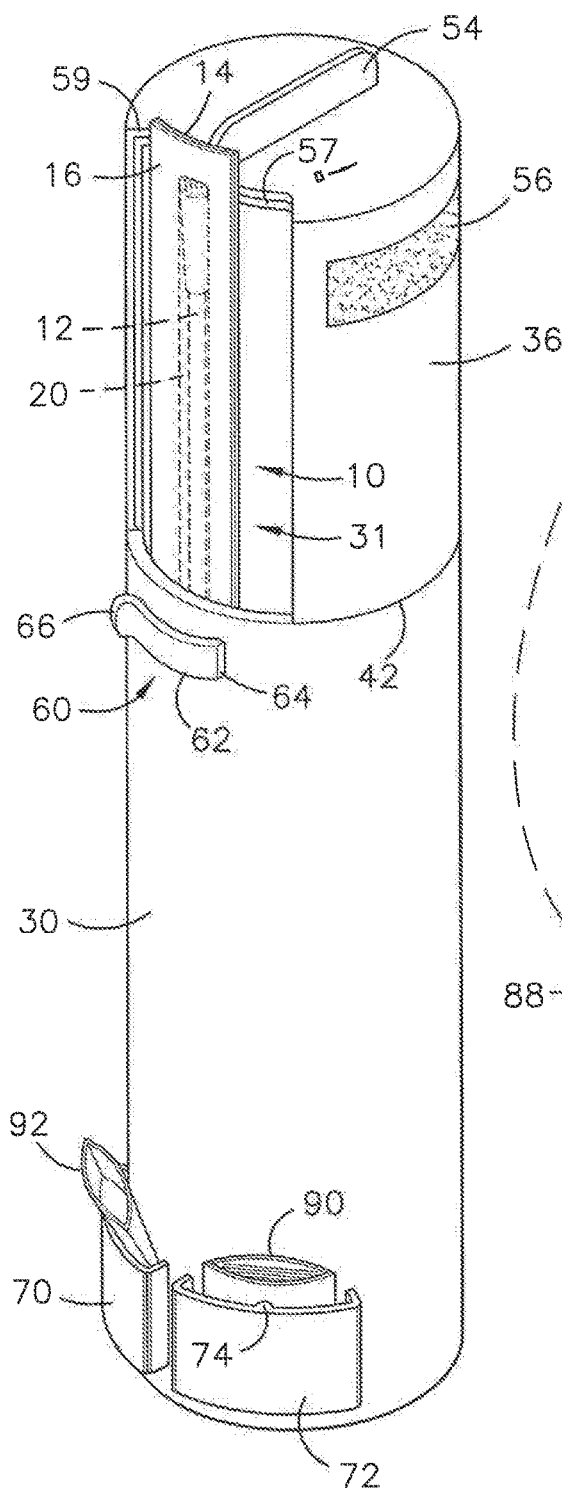
FIG. 10 is a pictorial view of the cylindrically shaped caddy of FIG. 3 in open condition showing a catheter package extending from inside the caddy body through the caddy body opening with the openable end of the catheter package extending through the caddy body opening to outside the caddy body and pulled to extend partially out of the caddy so the openable end of the catheter package is above the top of the caddy body.

When a user of the caddy needs a urinary catheter, the user rotates cap 36 to open position so that the user can reach with his or her fingers into cylindrical caddy body 30 and select a catheter package grabbing the upper portion of such selected catheter package and pulling the openable end and adjacent top portion of the selected catheter package out of the cylindrical caddy body 30 through the aligned caddy opening 32 and cap opening 38. The user then pulls the openable end and an adjacent portion of the catheter package out of the cylindrical caddy body 30 as shown in FIG. 10, so the openable end 22 of the catheter package 10 is above the top of the caddy and is accessible to a user. The user can then grasp the top of the sides 14 and 16 of the package at the openable end 22 of the package and start to peel the sides of the top portion of the package apart as shown in FIG. 2. With the preferred orientation of the catheter packages in the cylindrical caddy body 30, when the catheter package is pulled partially out of the cylindrical caddy body 30 and the top portion of the package is peeled apart, the plastic side 14 having the channel 20 for the catheter will be positioned between the catheter and the caddy to protect the catheter and keep it sterile. While the catheter may bend forward a bit, it will still be sterile as long as it is kept up in the caddy substantially cradled in the channel 20 in the plastic packaging 14 or at least with the plastic packaging 14 remaining between the catheter and the caddy so the catheter does not touch the caddy. The paper like side 16, which will be facing away from the caddy, will be peeled away from the plastic side 14 to partially open the catheter package as shown in FIGS. 2, 11, and 12. The side away from the caddy, usually the paper like side 16, can then be moved outwardly and downwardly from plastic side 14 and from the opening in the caddy as indicated by the broken line arrow 88 in FIG. 11, and secured in the package material holder 60, as shown in FIGS. 11 and 12. As shown, the paper like side 16 can be slid sideways along tapered end 66 of spring tab 62 and held by spring tab 62 against cylindrical caddy body 30. Generally, by holding the side of the package as shown in FIGS. 11 and 12, such side will hold the lower portion of the catheter package 10 still in the caddy, in the caddy with the other open side of the package remaining between the now exposed portion of the catheter and the caddy to maintain the extended catheter in sterile condition. Now, if not already done, a packet 90 of sterile cleaning wipes can be opened, squeezed to condition it to stay open, and placed in caddy pocket 72, and a packet 92 of sterile lubricating gel can be opened, squeezed to condition it to stay open, and placed in caddy pocket 70. Care should be taken not to touch the opening and edges of the opening of the packets.

The user is now ready to perform the catheterization. Up to this point, the user will be touching various nonsterile surfaces and will not be worried about keeping sterile hands. The user will not yet have actually touched the catheter, although the user has touched the catheter package and has opened the catheter package and has gotten to the condition indicated in FIG. 11 where the catheter is being held in sterile condition by the caddy ready for the catheterization. The user, preferably with sterile gloves, can grab a sterile cleaning wipe from the sterile cleaning wipe packet and carefully clean the body area around the urethra where the catheter is to be inserted. The user will now generally re-glove with sterile gloves. With the sterile gloves on, the user can now grab the extended portion of the catheter as shown in FIG. 12 and pull the catheter from the package as shown by broken line 94. The side of the package, preferably paper like side 16, held in the holder 60 will generally hold the portion of the package still in the caddy, in the caddy so the package does not come out of the caddy with the catheter as the catheter is pulled from the package and from the caddy. The catheter is now in the user's hand as shown in FIG. 12 and can then be manipulated as desired by the user. As shown by broken line arrow 96 in FIG. 12, with a lubricating gel packet 92 open and in position in the gel packet holding pocket 70, the end of the catheter to be inserted into the urethra can be carefully inserted into the open lubricating gel packet 92 to be covered with lubrication gel. The catheter can then be moved to and with the user's gloved hands be inserted into the urethra.

After the catheterization is completed and the bladder drained, the catheter is generally removed from the urethra. The side of the now empty catheter package, shown as paper like side 16 in FIG. 12, can be removed from package material holder 60 by sliding it from end 66 of spring tab 62, and the empty catheter package can be pulled from the cylindrical caddy body 30. The removed used catheter can be placed in the empty catheter package and disposed of in normal manner, or the used catheter and empty catheter package can be separately disposed of. The cap 36 is now rotated to closed position and the caddy remains closed with a supply of catheters therein and ready for the next catheterization when needed. When the caddy becomes empty or low on packages of catheters, the caddy can be opened and new packages of catheters added to the caddy.

Figure 14:
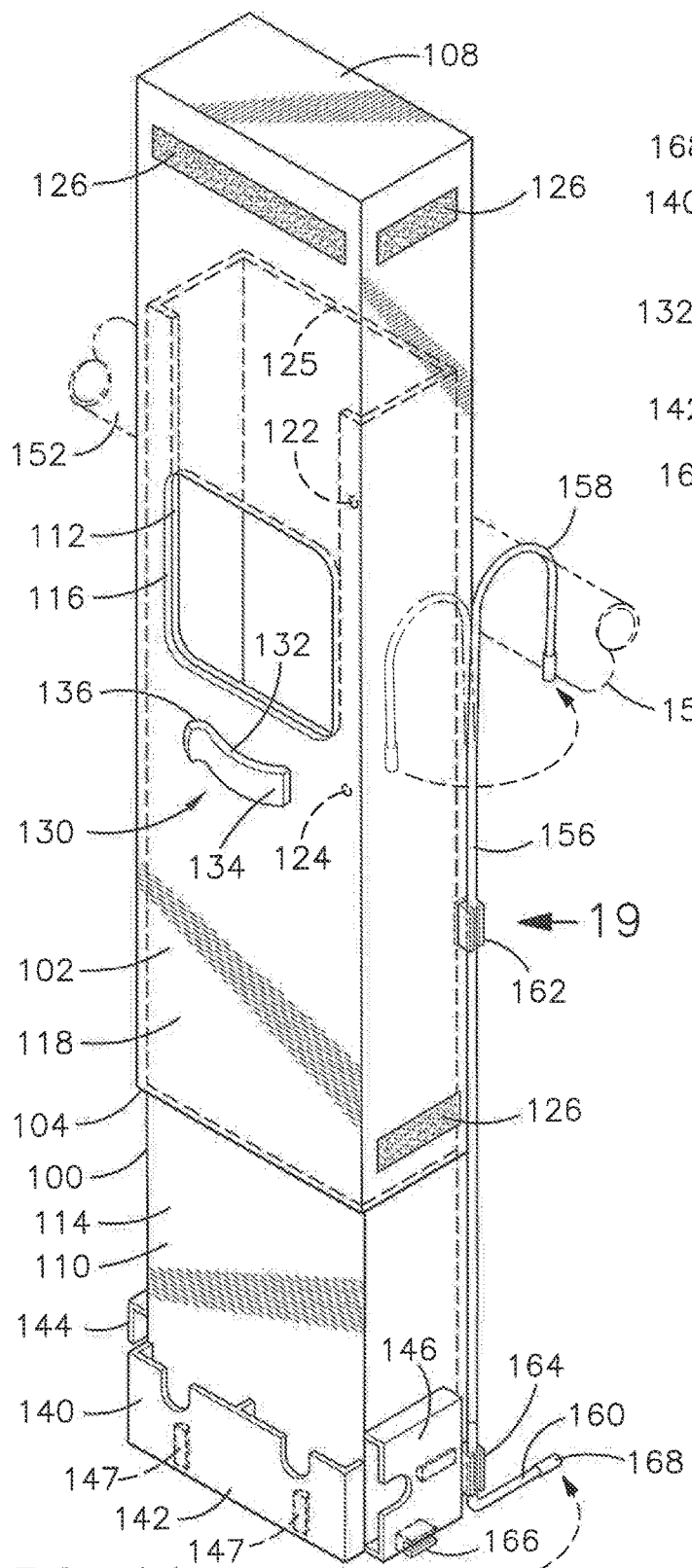
FIG. 14 is a pictorial view of a rectangular shaped catheter caddy of the invention in open condition.
Figure 21:
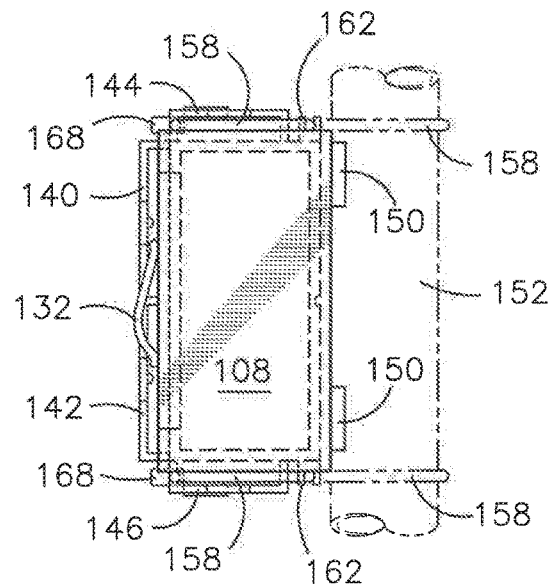
FIG. 21 is a top plan view of the rectangular caddy as shown in FIG. 16.
Figure 15:
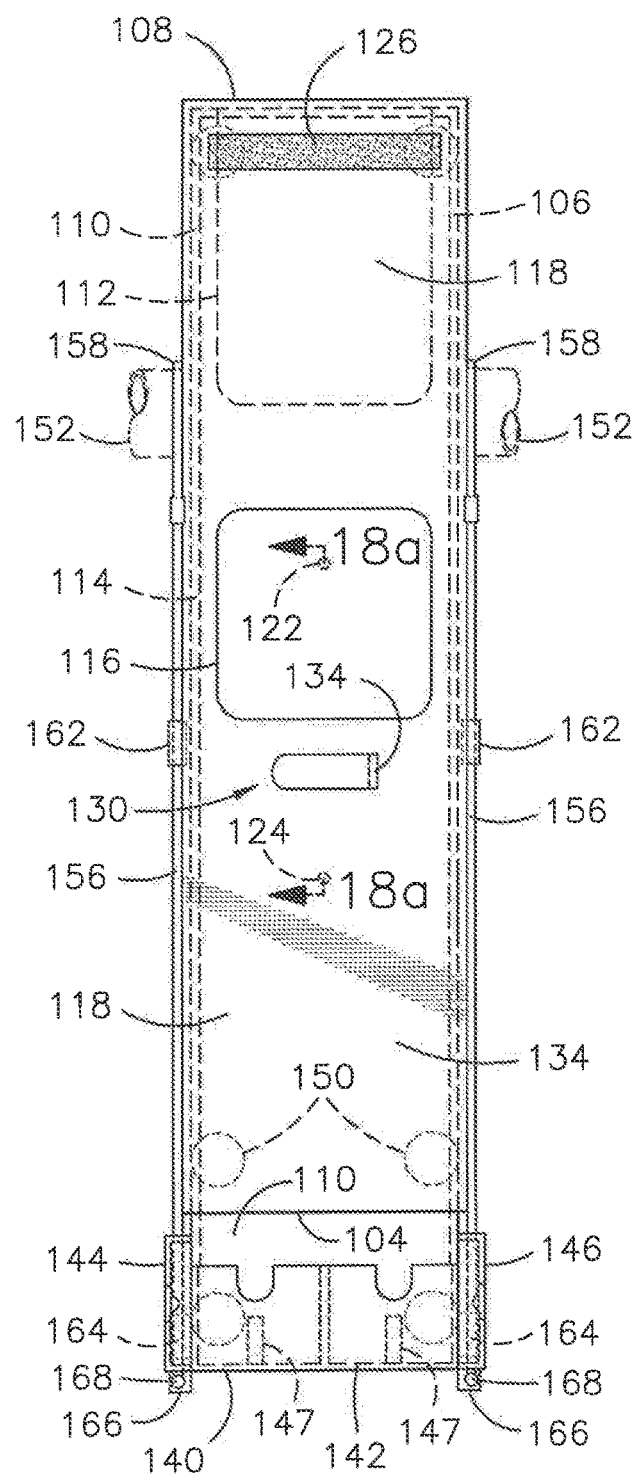
FIG. 15 is a front elevation of the catheter caddy of FIG. 14, but in closed condition.
Figure 16:
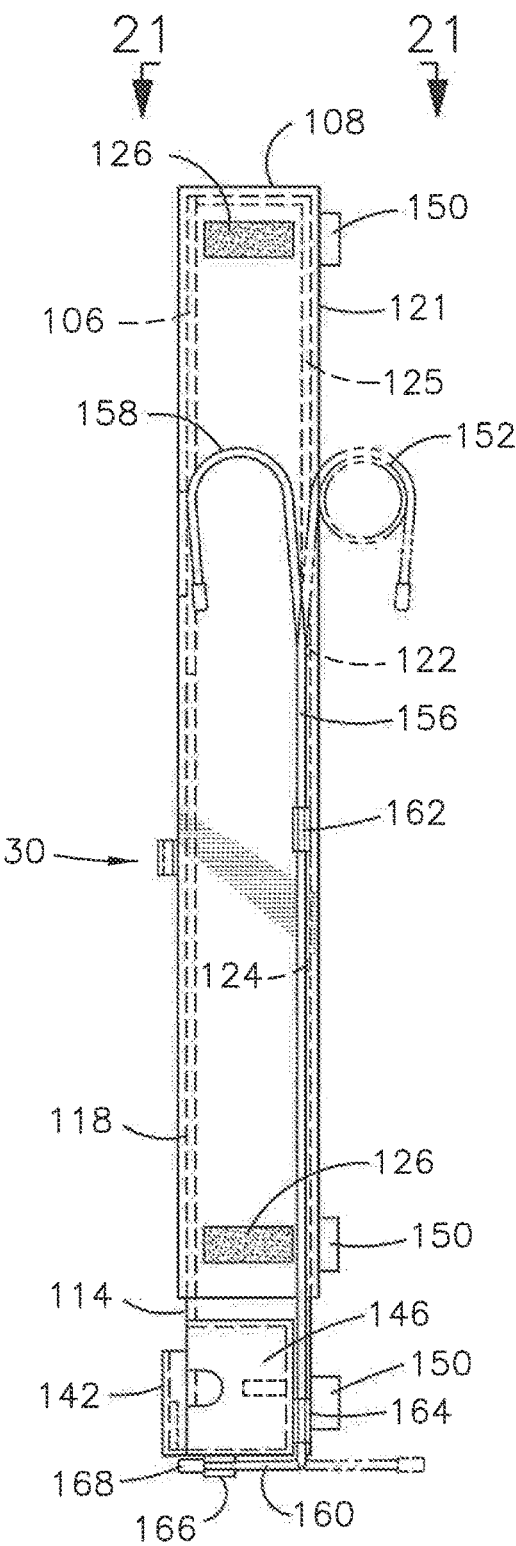
FIG. 16 is a side elevation of the catheter caddy of FIG. 15 in closed condition.

In a second embodiment of the invention, the caddy may be of rectangular shape as shown in FIGS. 14-23 having a rectangular main caddy body 100 and a rectangular outer caddy body 102 slidably received over a portion of the main caddy body 100. In the illustrated embodiment of FIGS. 14-23, the rectangular outer caddy body 102 has an open outer caddy body end 104 (lower end as shown in the orientation of FIGS. 14-17) which can receive therethrough an insertion end 106, FIGS. 14-17, of the main caddy body 100 so that the outer caddy body is slidably received over a portion of the main caddy body 100. The outer caddy body 102 has a closed outer caddy body opposite end 108 (upper end as shown in the orientation of FIGS. 14-17) which abuts the end of the insertion end 106 of the main caddy body 100 when the outer caddy body is slid over and along the main caddy body to a maximum extent as shown in FIGS. 15 and 16. With closed outer caddy body end 108 abutting the end of main caddy body insertion end 106, further sliding movement in that direction of outer caddy body 102 over main caddy body 100 is stopped. In such position, the caddy is considered in closed condition. Further, the lengths of main caddy body 100 and outer caddy body 102 are such that the end portion 110 of the main caddy body away from the insertion end, i.e., the lower end portion of the main caddy body 100 as shown in FIGS. 14 and 15, is never covered by the outer caddy body 102 and is always exposed outside of the outer caddy body 102. This end of main caddy body 100 will sometimes be referred to as the main caddy body exposed end portion 110. This main caddy body exposed end portion 110 provides a place for a user to hold the main caddy body 100 when the caddy is in closed condition so the outer caddy body 102 can be slid on the main caddy body to open condition and provides a convenient place where pockets for holding a packet containing sterile lubricating gel and a packet containing a sterile cleaning wipe can be placed.

Main caddy body 100 has a main caddy body opening 112, shown hidden in broken lines in FIG. 15 and shown as visible in FIGS. 14 and 17, through a side, here shown as front side 114 thereof, and positioned toward the insertion end 106 thereof. Outer caddy body 102 has an outer caddy body opening 116 through the corresponding and confronting side of the outer caddy body, here shown as front side 118 thereof, with a size and orientation substantially equal to the main caddy body opening 112. When the outer caddy body 102 is slid to the closed condition as shown in FIGS. 15 and 16, the outer caddy body opening 116 is closed by the confronting front wall 114 of the main caddy body 100 and the main caddy body opening 112 is closed by the confronting front wall 118 of the outer caddy body 102. The outer caddy body 102 can be slid along the main caddy body to an open condition where the outer caddy body opening 116 is aligned with the main caddy body opening 112, as shown in FIGS. 14 and 17. In this open condition, access is provided from outside the caddy through aligned outer caddy body opening 116 and main caddy body opening 112 into the interior of main caddy body 100. Outer caddy body 102 can be slid back and forth on main caddy body 100 between these open and closed conditions.

To resist free sliding movement of outer caddy body 102 back and forth along the main caddy body 100 and to hold the outer and main caddy bodies together in either open or closed condition, a projection 120 can be provided extending from a wall, such as extending inwardly from outer caddy body back wall 121 as shown in FIGS. 18*a* and 18*b*, which will mate with either of recesses 122 or 124 (hidden recesses shown in FIG. 17) in the outer surface of main caddy body back wall 125. FIGS. 18*a* and 18*b* are sections through portions of the respective back walls 121 and 125. Thus, when outer caddy body 102 is slid over main caddy body 100 to a closed condition as shown in FIGS. 15, 16, and 18*a*, projection 120 snaps into recess 122, FIG. 18*a*. When outer caddy body 102 is slid over main caddy body 100 to open condition, so that outer caddy body opening 116 is aligned with main caddy body opening 112, projection 120 snaps into receiving recess 124 (this position is not shown) to place and hold the rectangular caddy in open condition as shown in FIGS. 14 and 17. FIG. 18*b* shows how confronting back walls 121 and 125 will flex slightly to allow projection 120 to move back and forth between recesses 122 and 124. FIG. 18*b* shows projection 120 between recesses 122 and 124, meaning that outer caddy body 102 is in intermediate position between open and closed conditions. This condition will occur as the outer caddy body 102 is slid along main caddy body 100 between closed and open conditions. If outer caddy body 102 continues to be slid beyond the open condition wherein projection 120 is positioned in recess 124, outer caddy body 102 can slide completely off of main caddy body 100. However, once in open condition, projection 116 will hold outer caddy body 102 on main caddy body 100, unless forced to slide beyond that position. Patches of nonslip, gripping material 126 can be provided at various locations on the caddy body for a user to grip when opening or closing the caddy.

Figure 23:
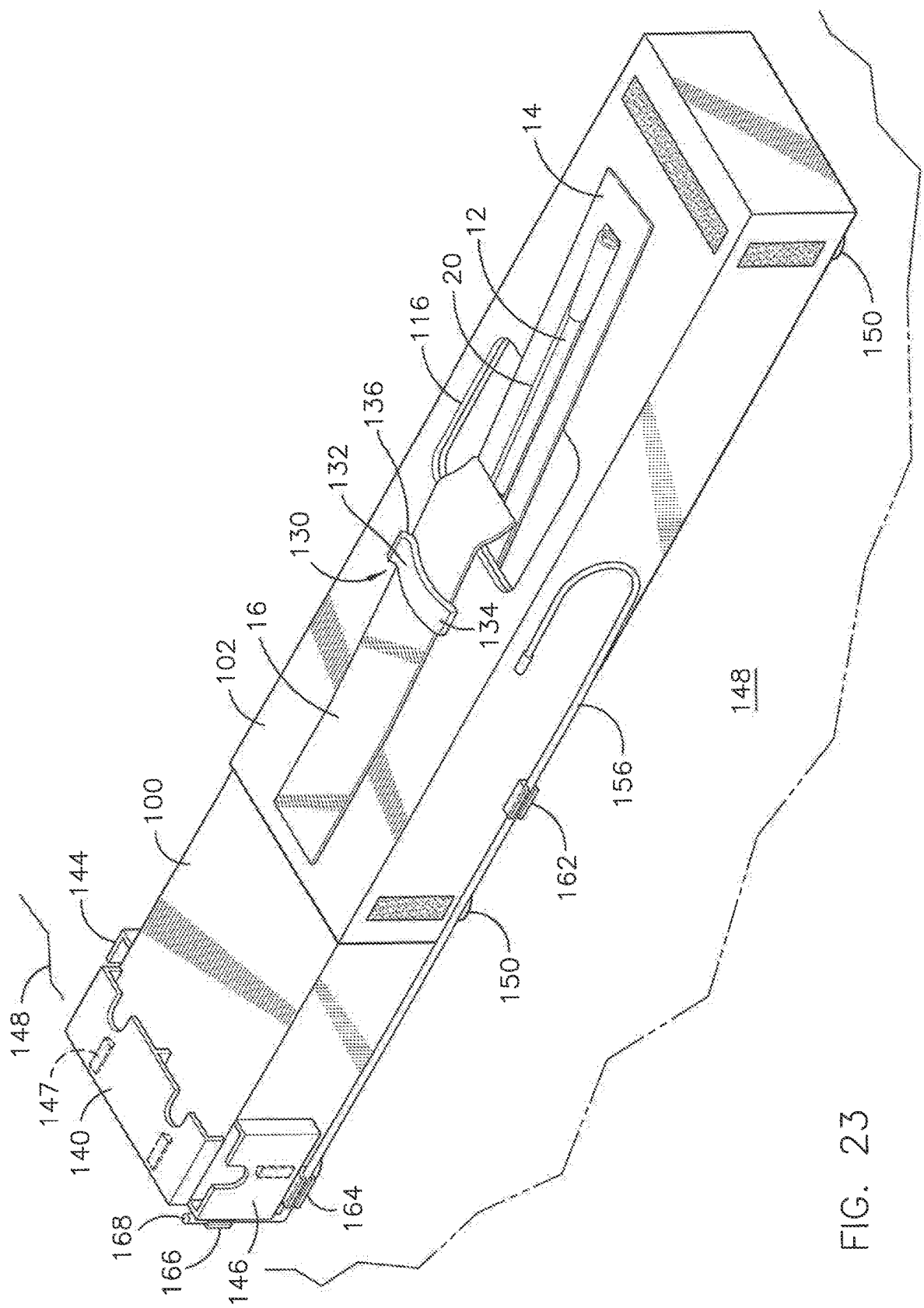
FIG. 23 is a pictorial view of the rectangular caddy as shown in FIGS. 14 and 17 in open condition resting in a horizontal orientation on a horizontal supporting surface.

As with the first embodiment of the caddy, a holder 130 in the form of a spring tab 132 is attached at one end 134 to outer caddy body 102 centered below outer caddy body opening 116. Spring tab 132 is biased against outer caddy body 102 with end 136 tapered away from against outer caddy body 102 to form an entrance for package sheet material such as the paper like or plastic material from the catheter package to be inserted and held between spring tab 132 and outer caddy body 102. If needed, the surface of spring tab 132 and/or outer caddy body 102 against which spring tab 132 abuts can be roughened or otherwise shaped to reduce sliding of the sheet material between the two, except when forced. In addition, main caddy body 100 may be provided with one or more, and preferably four, pockets 140, 142, 144, and 146 in a convenient location such as on the exposed end portion 110 of main caddy body 100 as shown in FIGS. 14-17. Similarly to the cylindrical embodiment, these pockets will be sized to receive and hold open an open packet of sterile catheter lubrication gel and a sterile packet containing a cleaning wipe. Pockets 140 and 142 are shown on the main body front wall 114 of the caddy and are oriented in the longitudinal axial direction of the caddy so when the caddy is in a vertical position as shown in FIGS. 14-22, such pockets face and open upwardly. Pockets 144 and 146 are located on opposite sides of the exposed end portion 110 of the caddy main body and are oriented transversely to the longitudinal axis of the caddy so when the caddy is placed substantially horizontally on a substantially horizontal surface, such as a counter top or table top as shown in FIG. 23, the pockets 144 and 146 face and open upwardly. The pockets will be sized to hold standard sterile gel packets in a slightly squeezed open condition and to hold standard cleaning wipe packets in a slightly squeezed open condition. As with the cylindrical caddy previously described, pockets 140, 142, 144, and 146, may include a ridge or bar 147 to more securely hold the packet within the pocket when the catheter or wipe is withdrawn from the packet.

The rectangular caddy is adapted to be used in either a vertical orientation as shown in FIGS. 14-22, or in a horizontal orientation, FIG. 23, with the caddy positioned on a substantially horizontal surface 148 such as a counter top or other substantially horizontal surface. The caddy will often be used to carry urinary catheters when a user is out and about so needs to be convenient to use in various locations, very often in public restrooms which may have a substantially horizontal countertop or shelf available on which the caddy may be placed in horizontal position or may have handicap railings where the caddy can be hung in a vertical position. Advantageously, the caddy can include slip resistant feet 150, FIGS. 15 and 16, shown on both ends of the back of outer caddy body 102 and on the back of the exposed end portion 110 of the main caddy body 100 to support and stabilize the caddy when placed in horizontal position on a counter top or other horizontal surface. In order to hang the caddy using a handicap railing, the railing should be a substantially horizontal railing. These are generally available in public restrooms, with a fragmentary section of such a railing being shown in broken lines as 152 in FIGS. 14-17 and 21.

In order to hang and easily operate the caddy in hanging position, the illustrated rectangular caddy can be provided with a pair of hanging hooks each having a loop portion 158 extending from one end of a shank portion 156 with a spacer arm portion 160 extending from the opposite end of the shank and aligned with the loop portion 158. The shank portion 156 of the hooks are rotatably mounted to the sides of the caddy by clips 162 on outer caddy body 102 and clips 164 on the exposed portion 110 of main caddy body 100 so that the shank portions 156 of the hooks can be rotated in clips 162 and 164 to rotate the loop portions 158 at the upper ends of the shanks 156 and the spacer arm portions 160 at the lower ends of the shanks 156 to extend rearwardly from the caddy as shown in FIG. 14 and shown in broken lines in FIG. 16 when desired to hang the caddy from the railing. When the hooks are not in use to hang the caddy, the shank portions 156 are rotated in clips 162 and 164 so that the loop portions 158 at the upper ends of the shanks 156 and the spacer arm portions 160 at the lower ends of the shanks 156 are positioned out of the way against the sides of the caddy as shown in solid lines in FIG. 16 and are held in this out of the way position by clips 166 which hold spacer arm portions 160. Clips 162, 164, and 166 can be molded on the outer caddy body 102 and main caddy body 100 or glued or otherwise attached to the outer and main caddy bodies. Clips 162 and 164 receive the shank portion 156 of a hook and hold the shank portion so it can rotate in the clips and so that the clips 162 can slide along the shank when the outer caddy body is slid along the main caddy body. Spacer arm portions 160, when extending rearwardly from the caddy as shown in solid lines in FIG. 14, will hold the lower portion of the caddy away from a wall behind the handicap railing on which the caddy is hung to hold the caddy in a substantially vertical orientation when hung on a handicap railing. Handicap railings are generally spaced about one and one-half inches from a wall. Therefore, in order to orient the caddy vertically when hanging on a handicap railing, the spacer arm 160 of the hook can be made longer than the loop portion of the hook to extend to or closer to the wall from which the handicap railing is spaced. However, the caddy will still be considered as substantially vertical if the spacer arm portions extend behind the caddy only as far as the hook portion, generally the case, or even if the spacer arm portions are not provided. The ends of spacer arms 160 can be provided with spacer arm tips 168 of a resilient material such as a resilient plastic so as to not mar walls against which such tip ends may abut. While the hooks have been described as hanging the caddy on a handicap railing, they can also be used to hang the caddy on the top edge of a cabinet door, on the top edge of a stall door in a restroom stall, or a similar edge that might be available in a particular environment.

Figure 20:
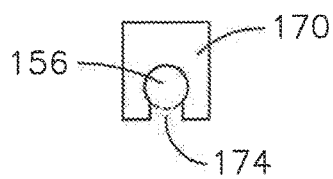
FIG. 20 is a top view of the hook clip of FIG. 19.
Figure 19:
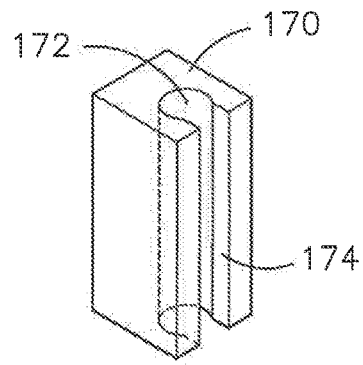
FIG. 19 is a pictorial view of a hook clip as indicated in FIG. 14.

Clips 162, 164 and 166 can be of various configurations, with a configuration as shown in FIGS. 19 and 20 having been found satisfactory. As shown in FIGS. 19 and 20, the clips may be molded of a resilient material 170 and have a cylindrical passage 172 extending longitudinally within the clip with a slot 174 opening along the longitudinal passage. The resilient material will deflect enough to enlarge the slot 174 along the longitudinal passage to allow the shank portion 156 of the hook to be pushed into the cylindrical passage 172 where it will then be held as shown in FIG. 20. The resilient material will allow the shank portion 156 to rotate in the cylindrical passage and may be tight enough to resist rotation of and sliding of the shank portion to some extent (prevent free rotation and sliding) except when forced by a user. Similarly, clip 166 will allow a portion of the spacer arm portion 160 of the hook to be pushed through slot 174 into passage 172 when the hook is moved to position along the side of the caddy to keep it out of the way. That portion of the spacer arm portion can be pulled out of the passage 172 when desired to rotate the loop portion of the hook to extend rearward from the caddy to hang the caddy. The resilient material of the respective clips can be selected so that each of the clips can have a different resiliency to make it easier, for example, to push and pull the portion of the spacer arm portion into and out of clip 166 to hold or release it along the side of the caddy than it is to pull the shank portion out of clips 162 and 164. Further, clips 164 on the exposed portion of main caddy body 100 could be designed to prevent or resist sliding of shank portion 156 through passage 172 to prevent shank portion 156 from sliding along the sides of the caddy thereby keeping the loop portions 158 and the spacer portions 160 in the same position with respect to main body 100 when the loop portion 158 and spacer portion 160 are extended rearwardly from the caddy. Clips 162 would be free to slide along shank portion 156 so that outer caddy body 102 can slide between closed and open conditions with respect to main caddy body 100. Further, an additional clip could be provided to hold loop portion 158 when rotated along the side of the caddy. This could be in place of clip 166 or in addition to clip 166. If a clip is provided for the loop portion 158, such loop portion would have to be released when sliding the caddy between closed and open conditions. Alternately, the hook could be mounted to and attached solely to the outer caddy body or to the main caddy body.

To prepare the rectangular caddy of FIGS. 14-23 for use, outer caddy body 102 is slid along main caddy body 100 so that the caddy is in open condition with outer caddy body opening 116 aligned with main caddy body opening 112 thereby creating an opening through outer caddy body opening 116 and aligned main caddy body opening 112 from outside the caddy to inside the main caddy body. Packages 10 of catheters can then be inserted through aligned openings 116 and 112 and arranged in main caddy body 100. Alternately, depending upon how the hooks are mounted on the caddy (in the illustrated embodiment the mounting of the hooks would interfere with removal of the outer caddy body 102 from the main caddy body 100), and how the main and outer caddy bodies are held together in open and closed conditions, outer caddy body 102 may be able to be slid completely off the main caddy body insertion end 106 of main caddy body 100 to expose the open insertion end 106 of main caddy body 100. Packages 10 of catheters can then be inserted through the open insertion end 106 directly into the main caddy body 100 and arranged in main caddy body 100. In either case, the catheter packages 10 will be oriented with the openable end 22 of the packages 10 toward the insertion end 106 of the main caddy body 100. FIG. 22 is a section through the caddy in open condition showing a plurality, here twelve, of packages 10 of urinary catheters 12 positioned in main caddy body 100 for storage and carrying of such packages. The catheter packages 10 will preferably be arranged with the opaque paper like side 16 facing the aligned openings 112 and 116, although they could be arranged oppositely. Once catheter packages 10 are inserted into catheter body 100 through aligned outer caddy body opening 116 and main caddy body opening 112, or through the open insertion end 106 of the main caddy body 100, the user will generally slide outer caddy body 102 along main caddy body 100 to closed position to close main caddy body opening 112 for storage and carrying of the catheter packages 10 in a closed caddy.

When a user of the caddy needs a urinary catheter, the user slides outer caddy body 102 along main caddy body 100 to open position so that the user can reach into main caddy body 100 and select a catheter package grabbing the openable end portion of such selected catheter package and pulling the openable end portion of the selected catheter package out of the caddy through the aligned main caddy body opening 112 and outer caddy body opening 116. The user then pulls the openable end and a portion of the catheter package out of the caddy as shown in FIG. 23, so the openable end 22 of the catheter package 10 is outside of the caddy beyond an edge of the outer caddy body opening 116 and is accessible to a user. Then, as previously described, the user can grasp the ends of the sides 14 and 16 of the package at the openable end 22 of the package and start to peel the sides of the top portion of the package apart. With the preferred orientation of the catheter packages in the main caddy body 100, when the catheter package is pulled partially out of the outer caddy body opening 116 and the top portion of the package is peeled apart as shown in FIG. 23, the plastic side 14 having the channel 20 for the catheter will be positioned between the catheter and the caddy to protect the catheter and keep it sterile. With the catheter package 10 open, the catheter 12 will remain sterile as long as it is kept substantially cradled in the channel 20 in the plastic packaging 14 or at least with the plastic packaging 14 remaining between the catheter and the caddy so the catheter does not touch the caddy. The paper like side 16, which will be facing away from the caddy, will be peeled away from the plastic side 14 to partially open the catheter package as shown in FIG. 23. The side away from the caddy, usually the paper like side 16, can then be moved outwardly from plastic side 14 and from the opening in the caddy and secured in the holder 130, as shown in FIG. 23. The paper like side 16 can be slid sideways along tapered end 136 of spring tab 132 and held by spring tab 132 against outer caddy body 102. As previously indicated, by holding a side of the package in holder 130, such side will hold the lower portion of the catheter package 10 still in the caddy, in the caddy with the other open side of the package remaining between the now exposed portion of the catheter and the caddy to maintain the now exposed portion of the catheter in sterile condition. Now, if not already done, a packet 90 containing a sterile cleaning wipe can be opened, squeezed to condition it to stay open, and placed in either caddy pocket 142 or 146, depending upon the orientation of the caddy, and a packet 92 of sterile lubricating gel can be opened, squeezed to condition it to stay open, and placed in either caddy pocket 140 or 144, again depending upon the orientation of the caddy. Care should be taken not to touch the openings and edges of the openings of the packets.

The user is now ready to perform the catheterization. Similarly to the embodiment previously described, up to this point, the user will be touching various nonsterile surfaces and will not be worried about keeping sterile hands. The user will not yet have actually touched the catheter, although the user has touched the catheter package and has opened the catheter package and has gotten to the condition indicated in FIG. 23 where the catheter is being held in sterile condition by the caddy ready for the catheterization. The user, preferably wearing sterile gloves, can grab the sterile cleaning wipe from the sterile cleaning wipe packet and carefully clean the body area around the urethra where the catheter is to be inserted. The user will now generally re-glove with new sterile gloves. With the sterile gloves on, the user can now grab the exposed portion of the catheter as shown in FIG. 23 and pull the catheter from the package. The side of the package, preferably paper like side 16, held in the holder 130 will generally hold the portion of the package still in the caddy, in the caddy so the package does not come out of the caddy with the catheter as the catheter is pulled from the package and from the caddy. The catheter is now in the user's hand and can then be manipulated as desired by the user. With a lubricating gel packet 92 open and in position in one of the gel packet holding pockets, the end of the catheter to be inserted into the urethra can be carefully inserted into the open lubricating gel packet to be covered with lubrication gel. The catheter can then be moved to and inserted into the urethra.

After the catheterization is completed and the bladder drained, the catheter is generally removed from the urethra. The side of the now empty catheter package, shown as paper like side 16 in FIG. 23, can be removed from holder 130 by sliding it from end 136 of spring tab 132, and the empty catheter package can be pulled from the caddy. The removed used catheter can be placed in the empty catheter package and disposed of in normal manner, or the used catheter and empty catheter package can be separately disposed of. The outer caddy body is now slid to closed position and the caddy remains closed with a supply of catheters therein and ready for the next catheterization when needed. When the caddy becomes empty or low on packages of catheters, the caddy can be opened and new packages of catheters added to the caddy.

As indicated, urinary catheters for use by a male are usually between sixteen and eighteen inches in length and urinary catheters for use by a female are usually nine to twelve inches in length. Therefore, the caddy should be made in a male size to hold the longer male catheters and a shorter female size to hold the shorter female size catheters. The shorter catheter packages will rest in the bottom of the inside of the longer caddy body and in a different position in relation to the caddy body openings which make the shorter catheter packages harder to grab and manipulate in the longer caddy and such shorter catheter packages may not be held as well when extending from the caddy opening positioned for the longer catheters. With the cylindrical caddy for example, the cylindrical caddy for storing and dispensing male catheters may be about eighteen inches in length and the cylindrical caddy for storing and dispensing female catheters may be about twelve inches in length. Both may be about four inches in diameter. The access opening may be about three inches wide and about six inches in length. The cut out in the top of the cap and top of the caddy body in the cylindrical caddy may extend inwardly about one half inch. With the rectangular caddy for example, the rectangular caddy for male catheters may be about seventeen and one half inches in overall length when in closed condition (with outer body about fifteen and one quarter inches in length) and with an overall length of about twenty two and one half inches when in open condition. The rectangular caddy for female catheters may be about twelve inches in overall length when in closed condition (with the outer body about nine and three quarter inches in length) and with an overall length of about seventeen and one half inches when in open condition. The rectangular caddy may be about four inches wide and about two inches deep. The main caddy body opening and the outer caddy body opening may each be about three inches by three inches so that the opening into the rectangular caddy body when in open condition is about three by three inches.

The caddy of the invention can be used in any environment where a supply of urinary catheters is desired and such catheters are used. While the caddies have been described as for use by users carrying the caddy around with them, the caddies can be used in a home or professional setting such as a clinic or hospital. In such instances it can be beneficial to include the caddy mounted on a cart that can be moved to desired needed locations along with other medical supplies and equipment that might be needed.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. For example, while the package material holder is shown and described as a spring clip to hold the portion of the package material concerned between the clip and the caddy body, various other constructions of a package material holder could be used, the important aspect of the package material holder being to hold the package material extending from the opened portion of the catheter package to maintain the unopened portion of the catheter package in position so that the catheter can be completely removed from the catheter package without the user touching the package or caddy or other unsterile surface. Further, while the means to hold the caddy in open or closed condition is described as projections which fit into recesses when the caddy is in either open or closed condition, various other means can be used to hold the caddy in the open and closed conditions. Accordingly, it is not intended that the invention be limited, except as by the claims set forth below.

The invention claimed is:

1. A urinary catheter caddy for storing a plurality of packages of urinary catheters and for holding a selected one of the plurality of packages for dispensing of the urinary catheter from the selected one urinary catheter package when a urinary catheter is needed for use, each urinary catheter package stored in the caddy containing and enclosing in sealed condition a single urinary catheter and openable at an openable end of the urinary catheter package to expose an end of the urinary catheter contained in the package and with the urinary catheter package having an opposite end, the caddy configured to hold the selected package to allow opening of the selected package and removal of the catheter from the opened selected package, comprising:

a caddy body forming a storage space sized to receive and hold a plurality of packages of urinary catheters with the openable end of each urinary catheter package in an access portion of the storage space;

an access opening extending from outside the caddy body into the access portion of the storage space configured to provide access by a user to the openable end of a urinary catheter package carried within the storage space and allow a user to select one of the urinary catheter packages and pull the openable end and adjacent intermediate portion of the selected urinary catheter package through the access opening with the opposite end and intermediate portion adjacent the opposite end of the urinary catheter package remaining in the storage space and to open the openable end and adjacent intermediate portion of the selected urinary catheter package to expose a portion of the urinary catheter therein, opening of the package performed by separating sides of the urinary catheter package at the openable end and along the intermediate portion of the package adjacent the openable end to expose a portion of the catheter in the then opened urinary catheter package so the exposed portion of the catheter can be grasped by the user, a first separated side of the then opened urinary catheter package remaining between the caddy and the exposed portion of the urinary catheter and a second separated side extending through the access opening away from the caddy and the exposed portion of the urinary catheter so as to open the exposed portion of the urinary catheter to outside the caddy through the access opening where such exposed portion of the urinary catheter can be grasped by the user and pulled from the portion of the urinary catheter package still in the portion of the urinary catheter package remaining in the storage space; and a package material holder for receiving and holding a portion of the second separated side of the catheter package extending through the access opening away from the exposed portion of the urinary catheter and thereby holding the unseparated rest of the urinary catheter package in position in the access opening and storage space so that the user can remove the catheter from the portion of the urinary catheter package remaining in the access opening and storage space by holding the exposed portion of the urinary catheter and pulling the urinary catheter from the portion of the urinary catheter package remaining in the storage space without the urinary catheter touching the caddy or the outside of the urinary catheter package.

2. A urinary catheter caddy according to claim 1, wherein the package material holder comprises a spring clip having a portion thereof biased against the caddy body for holding a portion of the second separated side of the package between the spring clip and the caddy body.

3. A urinary catheter caddy according to claim 1, wherein the access opening is closable to close the storage space for storage of the packages of catheters in the storage space and openable to allow access to a package when a catheter is to be dispensed.

4. A urinary catheter caddy according to claim 3, wherein the caddy includes a second caddy body movably mounted with respect to the caddy body and having a second access opening of size and shape substantially corresponding to that of the access opening, said second caddy body movable to align the second access opening with the access opening to open the access opening and to cover the access opening to close the access opening.

5. A urinary catheter caddy according to claim 4, wherein the caddy body is cylindrical and the second caddy body is a cylindrical cap that rotatably fits over an end of the caddy body and is rotatable between a position wherein the second access opening is aligned with the access opening to place the caddy in rotated open condition and a position wherein the second access opening is not aligned with the access opening so that the second caddy body blocks the access opening to place the caddy in rotated closed condition.

6. A urinary catheter caddy according to claim 5, additionally including means for holding the second caddy body in the rotated open condition when rotated to the open condition and for holding the second caddy body in the rotated closed condition when rotated to the closed condition.

7. A urinary catheter caddy according to claim 4, wherein the caddy body is rectangular and the second caddy body is rectangular and sized to slidably fit over an end of the caddy body and is slidable between a position wherein the second access opening is aligned with the access opening to place the caddy in an open condition and a position wherein the second access opening is not aligned with the access opening so that the second caddy body blocks the access opening to place the caddy in closed condition.

8. A urinary catheter caddy according to claim 7, additionally including means for holding the second caddy body with respect to the caddy body in the open condition when slid to the open condition and for holding the second caddy body with respect to the caddy body in closed condition when slid to the closed condition.

9. A urinary catheter caddy according to claim 8, additionally including hooks for hanging the caddy from a horizontally extending edge.

10. A urinary catheter caddy according to claim 9, wherein the horizontally extending edge is selected from a handicap railing or a door edge.

11. A urinary catheter caddy according to claim 9, wherein the hooks are retractably mounted to the caddy whereby the hooks can be moved to an out of the way position except when in use to hang the caddy.

12. A urinary catheter caddy according to claim 11, wherein the hooks are rotatably mounted to an edge of the caddy body whereby the hooks can be rotated to a position to extend from the caddy body when used to hang the caddy or to a position wherein the hooks are against the sides of the caddy body when the hooks are not used to hang the caddy.

13. A urinary catheter caddy according to claim 1, additionally including at least one bracket for hanging the caddy in a substantially vertical position.

14. A urinary catheter caddy according to claim 13, wherein the bracket is detachably attached to the caddy body.

15. A urinary catheter caddy according to claim 1, additionally including a pocket outside the caddy body sized and configured to hold an opened packet of lubricating gel in opened position for insertion of an end of the catheter into the opened packet after removal of the catheter from the opened catheter package held in the caddy.

16. A urinary catheter caddy according to claim 15, additionally including a pocket outside the caddy body sized and configured to hold an opened packet containing a sterile wipe for access to the sterile wipe.

17. A urinary catheter caddy according to claim 1, additionally including a plurality of packages of urinary catheters in the storage space.

18. A urinary catheter caddy for storing a plurality of packages of urinary catheters and for holding a selected one of the plurality of packages for dispensing of the urinary catheter from the selected one urinary catheter package when a urinary catheter is needed for use, each urinary catheter package stored in the caddy containing and enclosing in sealed condition a single urinary catheter and openable at an openable end of the urinary catheter package to expose an end of the urinary catheter contained in the package and with the urinary catheter package having an opposite end, the caddy configured to hold the selected package to allow opening of the selected package and removal of the catheter from the opened selected package, comprising:

a caddy body forming an elongate storage space having opposite ends and sized to receive and hold a plurality of packages of urinary catheters with the openable end of each urinary catheter package in an access portion of the storage space, said access portion being toward one of the opposite ends of the storage space;

an access opening extending from outside the caddy body into the access portion of the storage space configured to provide access by a user to the openable end of a urinary catheter package carried within the storage space and allow a user to select one of the urinary catheter packages and pull the openable end and adjacent intermediate portion of the selected urinary catheter package through the access opening with the opposite end and intermediate portion adjacent the opposite end of the urinary catheter package remaining in the storage space and to open the openable end and adjacent intermediate portion of the selected urinary catheter package to expose a portion of the urinary catheter therein, opening of the package performed by separating sides of the urinary catheter package at the openable end and along the intermediate portion of the package adjacent the openable end to expose a portion of the catheter in the then opened urinary catheter package so the exposed portion of the catheter can be grasped by the user, a first separated side of the then opened urinary catheter package remaining between the caddy and the exposed portion of the urinary catheter and a second separated side extending through the access opening away from the caddy and the exposed portion of the urinary catheter so as to open the exposed portion of the urinary catheter to outside the caddy through the access opening where such exposed portion of the urinary catheter can be grasped by the user and pulled from the portion of the urinary catheter package still in the portion of the urinary catheter package remaining in the storage space; and a package material holder for receiving and holding a portion of the second separated side of the catheter package extending through the access opening away from the exposed portion of the urinary catheter toward the side of the access opening away from the access portion of the storage space and opening the access opening from outside the caddy body to the exposed portion of the urinary catheter thereby holding the unseparated rest of the urinary catheter package in position in the access opening and storage space and opening the access opening to the exposed portion of the urinary catheter so that the user can remove the catheter from the portion of the urinary catheter package remaining in the access opening and storage space by holding the exposed portion of the urinary catheter and pulling the urinary catheter from the portion of the urinary catheter package remaining in the storage space without the urinary catheter touching the caddy or the outside of the urinary catheter package, said package material holder being positioned on the outside of the caddy body between the access opening and the end of the caddy body coinciding with the storage space end opposite the access portion.

19. A urinary catheter caddy according to claim 18, wherein the package material holder comprises a spring clip having a portion thereof biased against the caddy body for holding a portion of the second separated side of the package between the spring clip and the caddy body.

20. A urinary catheter caddy according to claim 19, wherein the spring clip includes an end thereof tapered away from the caddy body to receive and pass the portion of the second separated side of the package to be held by the spring clip into the portion of the spring clip biased against the caddy body.

\* \* \* \* \*